US011529498B2

(12) United States Patent
Kujawa et al.

(10) Patent No.: US 11,529,498 B2
(45) Date of Patent: Dec. 20, 2022

(54) RETRACTABLE NEEDLE CATHETER DELIVERY APPARATUS

(71) Applicant: SkyDance Vascular, Inc., Pleasant Grove, UT (US)

(72) Inventors: John Kujawa, Jupiter, FL (US); Michael Anstett, Safety Harbor, FL (US); William Bold, Delray Beach, FL (US)

(73) Assignee: SkyDance Vascular, Inc., Pleasant Grove, UT (US)

( * ) Notice: Subject to any disclaimer, the term of this patent is extended or adjusted under 35 U.S.C. 154(b) by 0 days.

(21) Appl. No.: 17/244,871

(22) Filed: Apr. 29, 2021

(65) Prior Publication Data

US 2021/0244919 A1  Aug. 12, 2021

Related U.S. Application Data

(63) Continuation of application No. PCT/US2020/061633, filed on Nov. 20, 2020.
(Continued)

(51) Int. Cl.
*A61M 25/06* (2006.01)
*A61M 25/00* (2006.01)
(Continued)

(52) U.S. Cl.
CPC .... *A61M 25/0631* (2013.01); *A61M 25/0075* (2013.01); *A61M 25/065* (2013.01);
(Continued)

(58) Field of Classification Search
CPC .......... A61M 25/0631; A61M 25/0075; A61M 25/065; A61M 25/0606; A61M 25/0111; A61M 39/26; A61M 2039/2426
See application file for complete search history.

(56) References Cited

U.S. PATENT DOCUMENTS 3,262,448 A   7/1966   Ring et al.
3,598,118 A   8/1971   Warren
(Continued)

FOREIGN PATENT DOCUMENTS

WO   WO-2018213148 A1   11/2018
WO   WO-2021108274 A1   6/2021

OTHER PUBLICATIONS

Co-pending U.S. Appl. No. 17/244,898, inventors Kujawa; John et al., filed Apr. 29, 2021.
(Continued)

*Primary Examiner* — Nilay J Shah
*Assistant Examiner* — Robert F Allen
(74) *Attorney, Agent, or Firm* — Wilson Sonsini Goodrich & Rosati

(57) ABSTRACT

A catheter insertion system includes a housing extending along a longitudinal axis. A needle extends distally from a distal end of the housing. The needle has a longitudinal passage coaxially aligned with the housing. A catheter has a length and is sized and shaped to be advanced from a retracted position within the longitudinal passage of the needle to an extended position with at least a portion of the catheter length extending beyond a distal tip of the needle. The needle is typically configured to be retracted back into the housing after the catheter has been advanced, thus providing an integrated catheter and catheter insertion apparatus. After needle retraction, the housing may be taped to the patient's skin while the needle remains protected within the housing. A luer on the catheter may then be connected to a fluid or other source in an otherwise conventional manner.

15 Claims, 21 Drawing Sheets

Related U.S. Application Data

(60) Provisional application No. 63/144,258, filed on Feb. 1, 2021, provisional application No. 63/023,699, filed on May 12, 2020, provisional application No. 62/985,182, filed on Mar. 4, 2020, provisional application No. 62/941,211, filed on Nov. 27, 2019, provisional application No. 62/941,541, filed on Nov. 27, 2019.

(51) Int. Cl.
| | |
|---|---|
| *A61M 25/01* | (2006.01) |
| *A61M 39/24* | (2006.01) |
| *A61M 39/26* | (2006.01) |
| *A61M 5/32* | (2006.01) |

(52) U.S. Cl.
CPC ..... *A61M 25/0606* (2013.01); *A61M 25/0111* (2013.01); *A61M 25/0637* (2013.01); *A61M 25/0693* (2013.01); *A61M 39/26* (2013.01); *A61M 2005/3235* (2013.01); *A61M 2039/2426* (2013.01)

(56) References Cited

U.S. PATENT DOCUMENTS

| | | | |
|---|---|---|---|
| 3,827,434 | A | 8/1974 | Thompson et al. |
| 3,921,631 | A | 11/1975 | Thompson |
| 4,037,600 | A * | 7/1977 | Poncy ............... A61M 25/0111 604/160 |
| 4,068,659 | A | 1/1978 | Moorehead |
| 4,772,264 | A | 9/1988 | Cragg |
| 4,957,489 | A * | 9/1990 | Cameron .......... A61M 25/0637 604/161 |
| 5,049,133 | A | 9/1991 | Villen Pascual |
| 5,098,389 | A * | 3/1992 | Cappucci ................ A61M 5/46 604/164.11 |
| 5,129,884 | A | 7/1992 | Dysarz |
| 5,685,852 | A | 11/1997 | Turkel et al. |
| 5,797,880 | A | 8/1998 | Erskine |
| 5,911,705 | A | 6/1999 | Howell |
| 5,935,110 | A | 8/1999 | Brimhall |
| 5,954,698 | A | 9/1999 | Pike |
| 6,443,926 | B1 | 9/2002 | Kletschka |
| 6,537,253 | B1 * | 3/2003 | Haindl ............... A61M 25/0631 604/164.01 |
| 6,547,762 | B1 * | 4/2003 | Botich ............... A61M 25/0631 604/110 |
| 7,740,615 | B2 | 6/2010 | Shaw et al. |
| 8,974,411 | B2 | 3/2015 | McKinnon |
| 9,162,037 | B2 | 10/2015 | Belson et al. |
| 10,238,840 | B2 | 3/2019 | Ishida |
| 10,525,236 | B2 | 1/2020 | Belson |
| 2002/0045843 | A1 * | 4/2002 | Barker ............... A61B 5/15003 600/585 |
| 2002/0169457 | A1 | 11/2002 | Quinn |
| 2003/0050601 | A1 | 3/2003 | Righi et al. |
| 2003/0120222 | A1 | 6/2003 | Vaillancourt |
| 2004/0116855 | A1 | 6/2004 | Popov et al. |
| 2005/0197635 | A1 | 9/2005 | Greydanus et al. |
| 2007/0225647 | A1 | 9/2007 | Luther et al. |
| 2008/0300574 | A1 | 12/2008 | Belson et al. |
| 2009/0264825 | A1 | 10/2009 | Cote et al. |
| 2009/0292272 | A1 | 11/2009 | McKinnon |
| 2011/0009849 | A1 | 1/2011 | Christensen et al. |
| 2012/0184910 | A1 | 7/2012 | Woehr |
| 2013/0178822 | A1 * | 7/2013 | Hickingbotham ............ A61B 17/3468 604/152 |
| 2015/0073304 | A1 * | 3/2015 | Millerd ............ A61B 5/150572 600/579 |
| 2015/0328434 | A1 | 11/2015 | Gaur |
| 2016/0045715 | A1 | 2/2016 | Galgano et al. |
| 2017/0209671 | A1 | 7/2017 | Ring |
| 2019/0076628 | A1 | 3/2019 | Anstett |
| 2019/0201667 | A1 | 7/2019 | Braithwaite et al. |
| 2019/0314614 | A1 | 10/2019 | Krause et al. |
| 2019/0328954 | A1 | 10/2019 | Hull |
| 2019/0351192 | A1 | 11/2019 | Bierman et al. |

OTHER PUBLICATIONS

PCT/US2020/061633 International Search Report and Written Opinion dated Mar. 26, 2021.
U.S. Appl. No. 17/244,898 Office Action dated Sep. 9, 2021.
U.S. Appl. No. 17/244,898 Notice of Allowance dated Oct. 25, 2021.
PCT/US2022/013928 International Search Report and Written Opinion of the International Searching Authority dated Apr. 11, 2022.

* cited by examiner

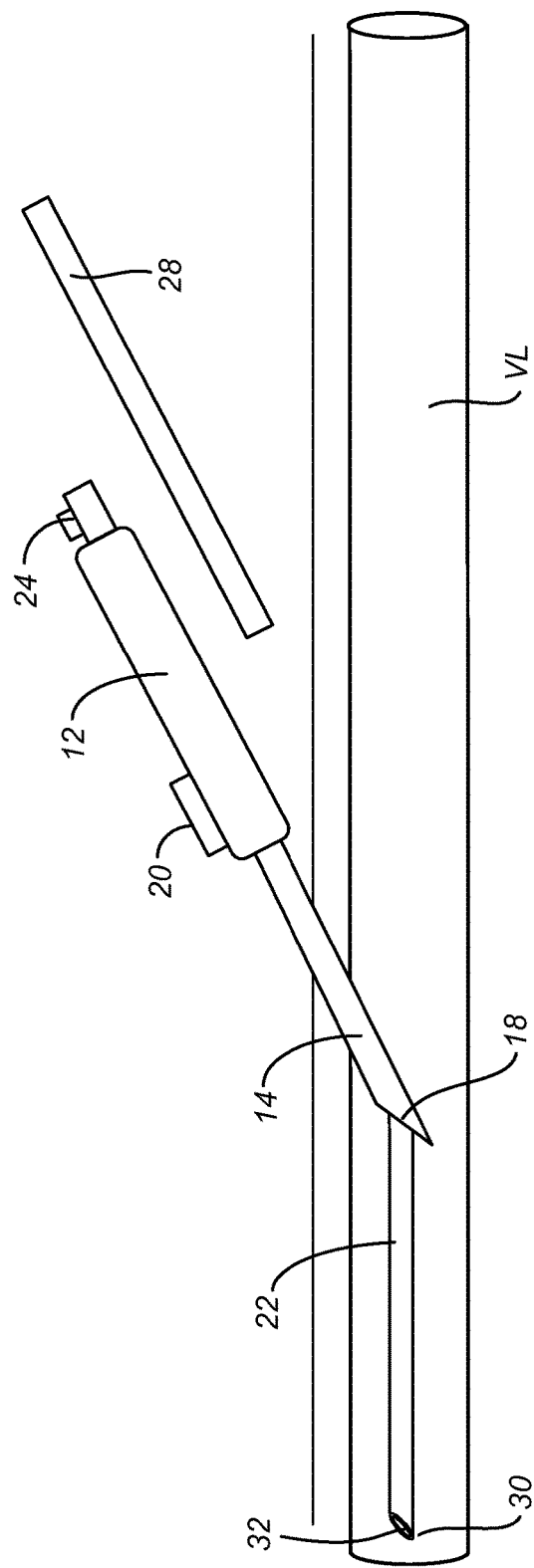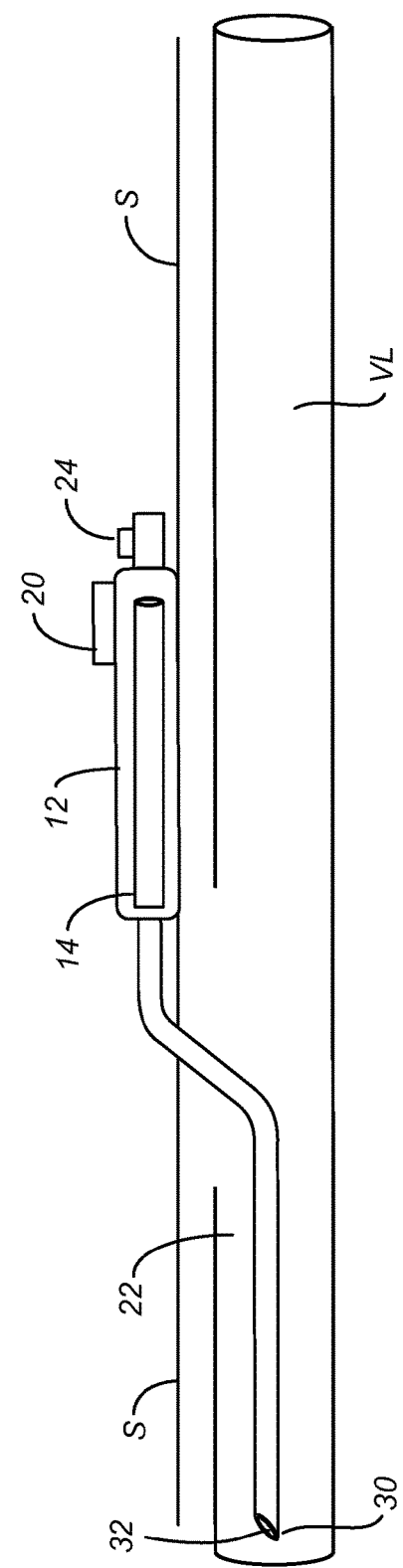

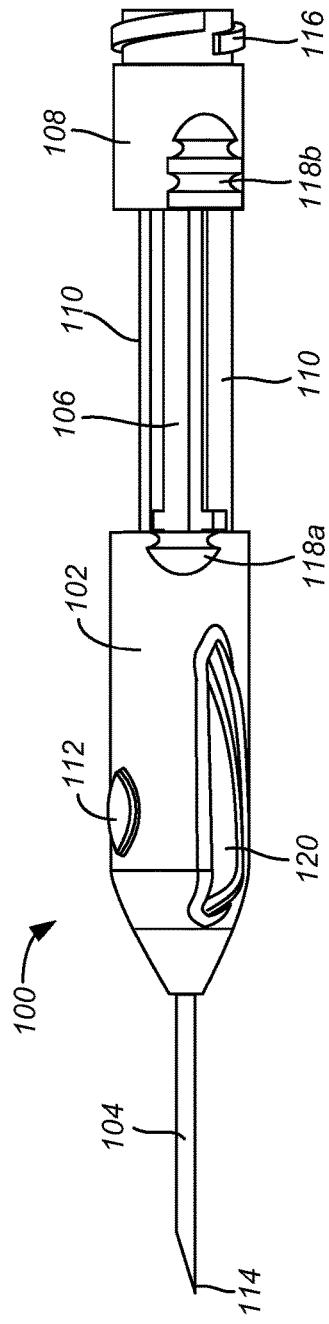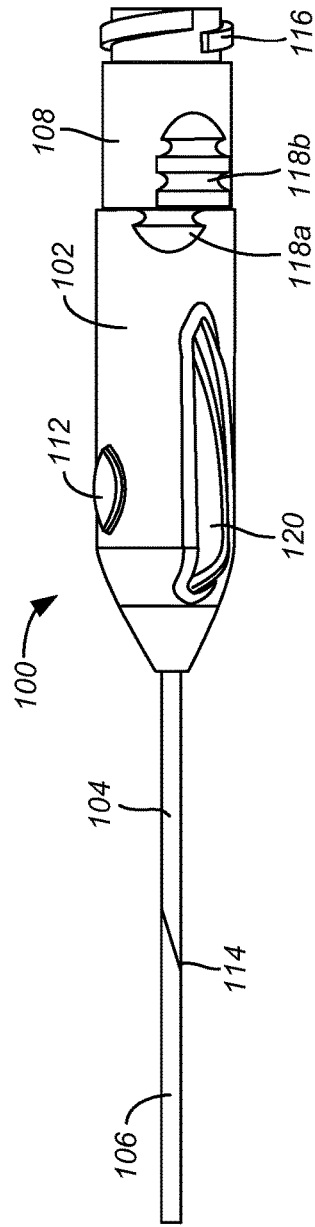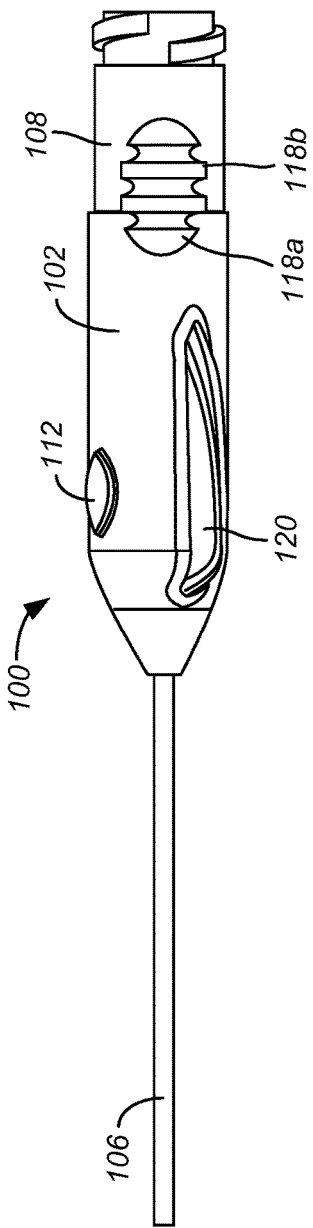

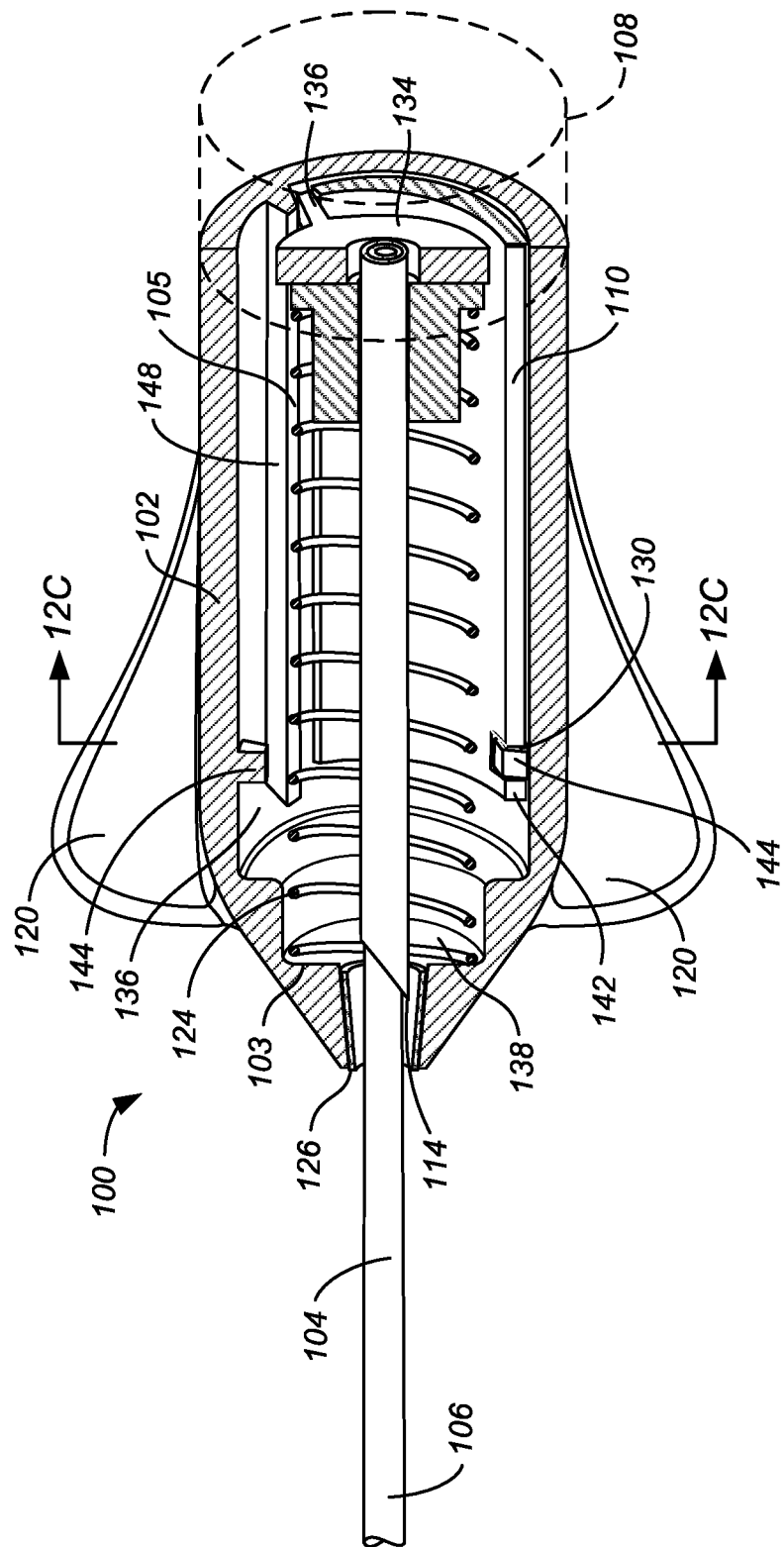

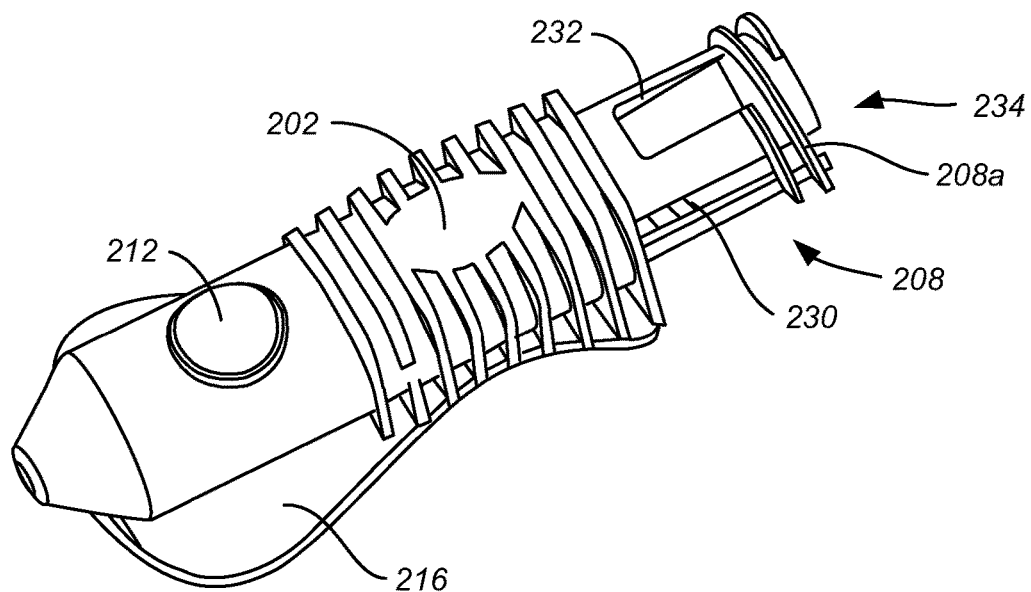
FIG. 15
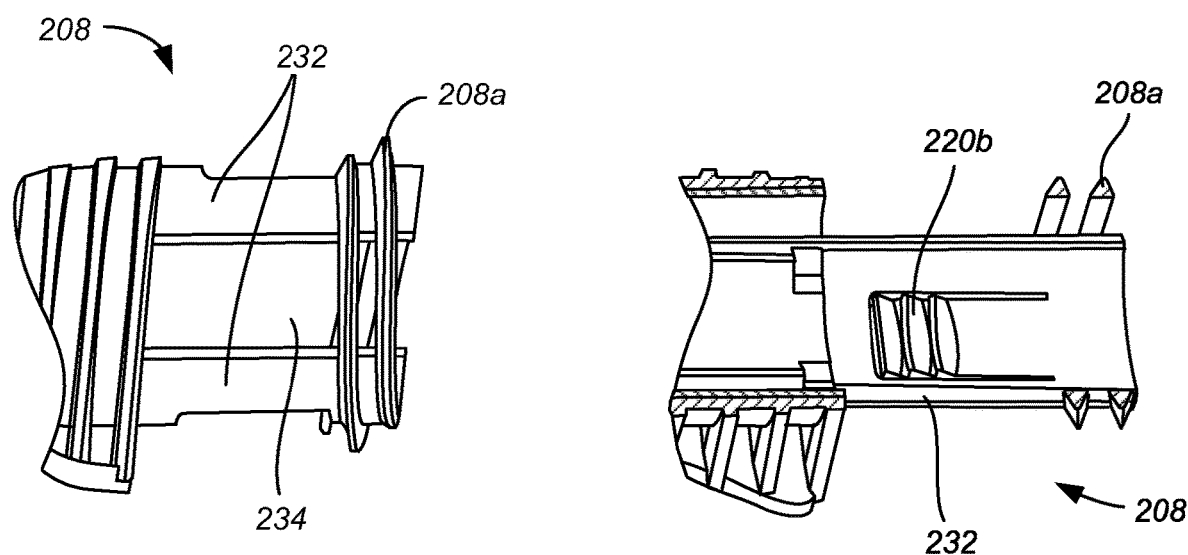
FIG. 15A
FIG. 15B

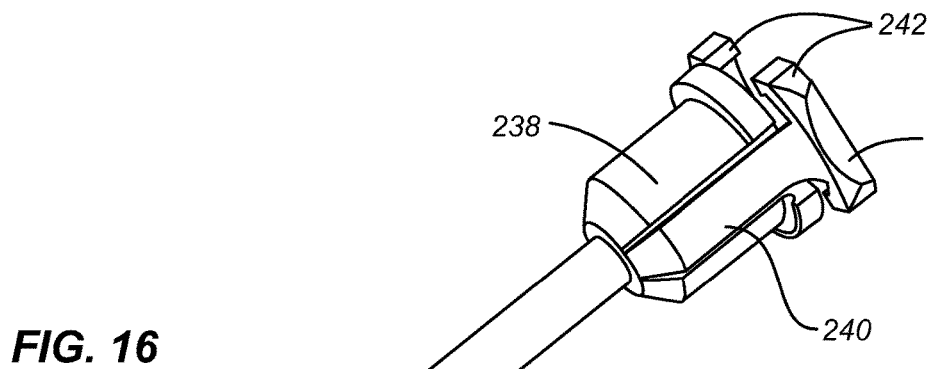
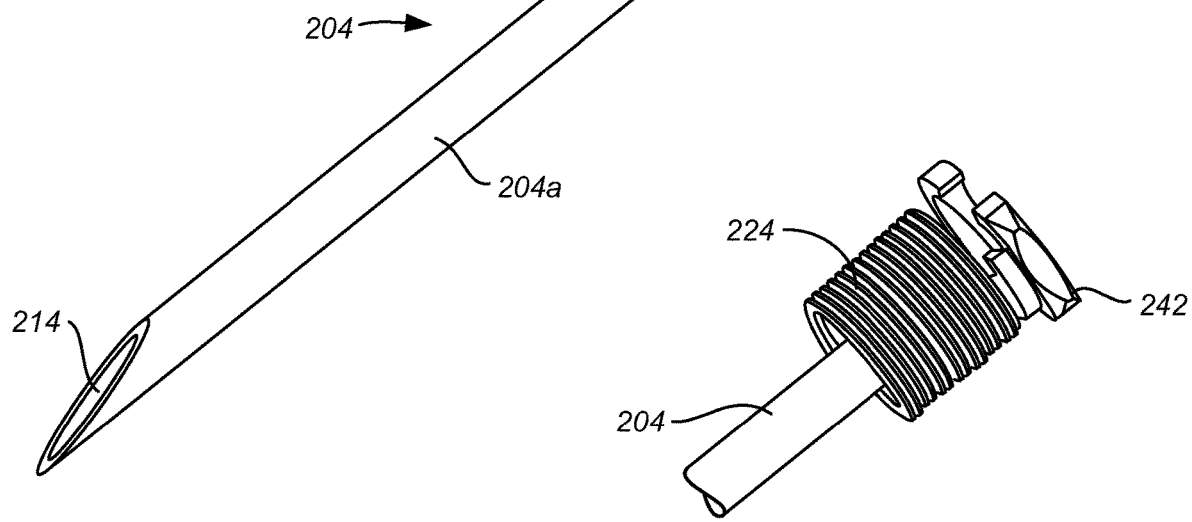
FIG. 16
FIG. 16C
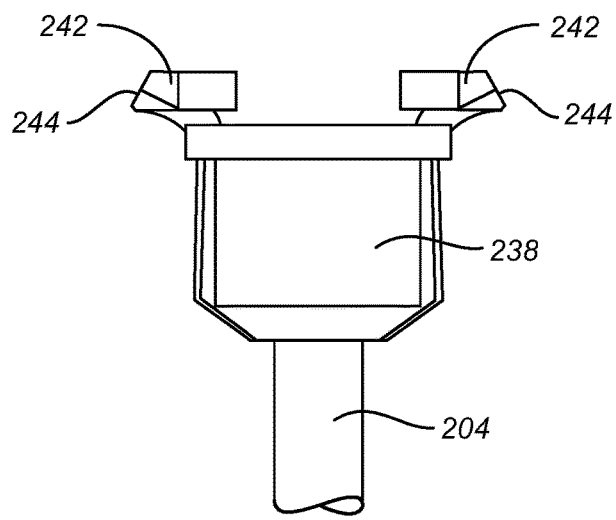
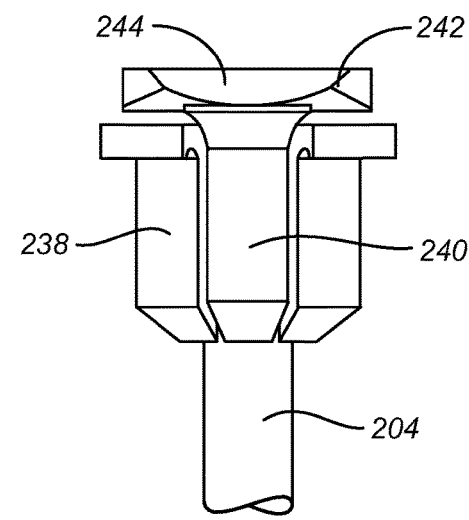
FIG. 16A
FIG. 16B

RETRACTABLE NEEDLE CATHETER DELIVERY APPARATUS

CROSS-REFERENCE TO RELATED APPLICATIONS

This application is a continuation of PCT Application No. PCT/US2020/061633, filed Nov. 20, 2020, which claims the benefit of U.S. Provisional No. 63/023,699, filed May 12, 2020; U.S. Provisional No. 62/985,182, filed Mar. 4, 2020; U.S. Provisional No. 62/941,541, filed on Nov. 27, 2019, and U.S. Provisional No. 62/941,211, filed on Nov. 27, 2019, the disclosures of which are fully incorporated herein by reference; this application also claims the benefit of U.S. Provisional No. 63/144,258, filed Feb. 1, 2021, the disclosure of which is fully incorporated herein by reference.

BACKGROUND OF THE INVENTION

1. Field of the Invention

The present invention relates generally to the field of medical devices and methods. More particularly, the present invention relates to catheter insertion devices, through-the-needle catheters, and related methods of their use.

Catheters are used in various medical procedures to administer fluids to a patient and/or to withdraw body fluids from a vein of a patient. Catheters are generally made of a flexible plastic material or various polymers, and a needle is used to access a vein or artery in the body in order to introduce the catheter into a blood vessel. One catheter insertion technique is known as the "through-the-needle" technique. In this technique, the needle is inserted through the skin and into the blood vessel until the needle tip is properly located in the vessel. Proper location of the needle tip is usually noted by a small flow of blood through the needle and into a flash chamber in a needle hub. After the needle is in proper position, a catheter is advanced through the needle and into the vessel. The needle is then withdrawn from the body, leaving the catheter implanted with the distal end of the catheter located in the vessel. However, typically, the needle cannot be easily removed and disposed of because of the interference of the catheter hub at the proximal end of the catheter. Accordingly, a common solution to this problem with the through-the-needle catheter is to remove the needle from the catheter by splitting the needle. For example, the needle may be made splittable by forming the needle of two longitudinally aligned halves, or by longitudinally scoring or perforating the body of the needle.

However, even with a splittable needle, the portions of the needle present a safety/disposal risk. Furthermore, the catheter is typically manipulated by an operator while threading the catheter through the lumen of the needle. As a result, catheters are often contaminated by bacteria from the skin of the patient or due to manipulation by the operator.

US2019/0076628, commonly assigned with the present application, describes a splittable needle catheter insertion tool where the catheter is held free from contamination prior to and during penetration of the needle to a patient's target vein. The design of the splittable needle catheter insertion tool is a significant advance in the art but still requires a separate needle/handle removal step during deployments as well as disposable of the needle at the point of use.

It would thus be desirable to provide needle-type catheter insertion tools which do not require splitting or other disassembly of the insertion tool at the time of catheter insertion. It would be further desirable that any such catheter insertion tools be inherently safe and non-traumatic to the patient in use, and in particular reduce any risk of accidental needle sticks to medical personnel as well as the patient. At least some of these objectives will be met by the inventions described and claimed below.

2. Listing of the Background Art

US2019/0076628 is described above. Other relevant patents and publications include U.S. Pat. Nos. 8,974,411; 4,957,489; US2017/0209671; US2019/328954; US2019/314614; US2019/351192; US2019/201667; US2009/264825; US2004/116855; U.S. Pat. Nos. 10,525,236; 10,238,840; 9,162,037; 5,935,110; 5,911,705; and 5,129,884.

SUMMARY OF THE INVENTION

In a first aspect, the present invention provides a catheter insertion system which includes both a catheter insertion device and a catheter to be inserted into a patient's venous system using the catheter insertion device. The catheter insertion device includes a housing extending along a longitudinal axis and a needle extending distally, usually coaxially, from a distal end of housing. The needle will typically have a longitudinal passage coaxially aligned with the longitudinal axis of the housing. The catheter will typically be configured (typically having a suitable length, diameter, and shaped) to allow the catheter to be advanced from a retracted position within the longitudinal passage in the needle to an extended position beyond a distal tip of the needle, typically having from 25% to 90%, usually from 50% to 75%, of the catheter length extending beyond the distal end of the needle when the catheter is in its extended position. The needle will be configured to be retracted back into the housing after the catheter has been distally advanced through the needle. In this way, the needle can be safely sequestered within the housing, and the housing can be secured to the patient, typically being taped or otherwise secured to a location on the patient's skin adjacent the catheter entry location.

In exemplary embodiments, the catheter insertion tool will further comprise a slider which is typically coupled to a proximal end of the needle. The slider maybe mounted on an outer surface of the housing so that a user may manually retract the needle in a proximal direction after the catheter has been advanced through the needle in a distal direction. In specific embodiments, the slider may be configured to be retracted through or within an axial slot on the housing. In many embodiments, the needle and/or the slider will be configured to prevent distal advancement of the needle after the needle has been retracted. In many instances, the catheter of the present invention will have an atraumatic distal tip. For example, the catheter may have a bullet tip where a port is formed within or through the bullet tip, typically by chamfering a hemispherical or other rounded surface of the bullet tip at an angle to provide a laterally deflected flow from the distal tip of the catheter. For example, the port may be chamfered or otherwise orientated at an angel from 35° to 75° relative to a longitudinal axis of the catheter were the distal end period.

In a particular aspect of the present invention, the venous or other luminal access catheter has a distal port configured to direct an outlet flow in a lateral direction (relative to the axial direction of the needle). The distal port has a fixed rotational orientation relative to the longitudinal axis of the housing. In this way, a user can readily control a rotational orientation of the distal port of the catheter as the catheter is being advanced from the needle. Usually, the user will rotationally orient the catheter insertion device which carries the catheter so that the distal port on the catheter is deployed in a desired rotational orientation in the venous lumen. Typically, the distal region of the catheter will be advanced against a wall of the venous lumen and the distal port will be oriented to direct fluid flow from the distal port toward the center of the venous lumen. Such orientation is advantageous as it promotes mixing of the fluid with a greater blood flow.

In other particular embodiments of the present invention, the port may be configured to orient the outlet flow at an angle in a range from 30° to 75° relatively to a longitudinal access of the catheter near its distal end.

In other specific aspects, the catheter may have an atraumatic tip, such as a bullet tip and the outlet port may be formed by a chamfer angled on one side of the bullet tip.

In a second aspect, the present invention provides a method for inserting a catheter into a vein. The method comprises manually advancing a needle extending distally from the housing into the vein. A catheter is manually advanced from the needle so that a distal port of the catheter lies at a desired location in a venous or other vessel lumen. The needle may then be manually retracted over the catheter and into the housing. After the catheter is thus deployed, the housing may be secured to a skin region of the patient, typically adjacent to the catheter insertion site, and a fluid source may be connected to a connecter at a proximal end of the catheter.

In particular method embodiments, the catheter has an atraumatic tip, such as a bullet tip, and the port may be formed by chamfering one side of the bullet tip, for example being oriented at an angle from 30° to 75° relative to a longitudinal axis of the catheter near the distal end. The methods may further comprise releasing a fluid from a non-longitudinally oriented port in a direction across a blood flow to promote mixing. For example, the distal region of the catheter will be advanced to lie along one side of a venous wall, where the user points the outlet port to direct fluid flow toward a center of the venous lumen, promoting mixing.

In still further aspects, the present invention provides an integrated catheter insertion apparatus comprising a housing, a needle, and a venous access catheter. By "integrated," it is meant that the housing, the needle, and the catheter are provided as a single assembly or structure. In particular, while various components of the single assembly will be rearranged during use, the components of the integrated apparatus are intended to be used together without disassembly and the apparatus will include a luer or other connector for subsequent attachment to external devices and equipment for both venous access for various purposes including delivery of intravenous fluids, drugs, blood transfusions, and the like as well as drawing blood and other treatments.

Any of these catheter insertion apparatuses may further comprising a valve in the luer or other proximal connector where the valve is configured to open in response to engagement with an external connector when the external connector is attached to the proximal connector. For example, the valve in the proximal connector may comprise a split valve that opens when advanced distally against a male rod or other fitting in an axial passage in the proximal connector.

In particular, a second exemplary embodiment of the catheter insertion apparatus according to the present invention comprise an integrated structure comprising housing having a longitudinal passage. A needle is slidably mounted within the longitudinal passage of the housing and has an axial lumen extending from a proximal end to a tissue-penetrating distal tip. A catheter is slidably mounted within the needle lumen and has a distal port and a proximal connector. In an initial configuration of the catheter insertion apparatus, the needle extends distally of the housing and the catheter is retracted proximally within the needle. The proximal connector of the catheter is distally advanceable to engage a proximal end of the housing. Such distal advancement extends the distal port of the catheter distally from the distal tip of the needle, and the needle is fully retractable over the catheter and within the housing after the catheter has been distally advanced.

In exemplary embodiments, the needle will typically have a length in a range from 0.5 cm to 3 cm, often having a length of 1.5 cm, but sometimes having a length or 1 cm or shorter. The catheter may have an exposed length (catheter tube length when fully extended distally from the housing) in a range from 2 cm to 8 cm, typically having an exposed length of 3 cm to 6 cm.

In particular embodiments, a spring assembly is disposed within the longitudinal passage of the housing and configured to retract the needle after the catheter has been distally advanced from the needle. Typically, the spring assembly is configured to automatically retract the needle after the catheter has been fully distally advanced from the needle. In specific instances, the spring assembly comprises a coiled spring disposed coaxially over the needle and a locking mechanism that holds the needle it its distally advanced position with the spring in an axially compressed configuration. Release of the locking mechanism allows the spring to axially expand, driving the needle proximally to retract the needle fully within the housing. In specific instances, the locking mechanism may be configured to automatically release the spring when the catheter is fully advanced and/or when the catheter retraction mechanism is actuated. Alternatively, in some embodiments, the spring assembly could be configured to be manually released, e.g. by a button or other trigger on the housing.

In further specific aspects, the catheter locks within the housing after the catheter has been fully advanced. In still other particular embodiments, the housing will be configured to be taped or otherwise secured to the patient after the needle has been retracted. In still further specific instances, the proximal connector of the catheter comprises a luer fitting for attachment to external structure, such as fluid delivery tubing, used in conventional medical systems.

In still further aspects of the present invention, a catheter insertion apparatus comprises a housing having a longitudinal passage. A needle assembly is slidably mounted within the longitudinal passage of the housing and has an axial lumen extending from a proximal carriage to a tissue-penetrating distal tip. Typically, a needle of the needle assembly extends distally from a distal end of the housing when the catheter insertion apparatus is in an initial configuration. The apparatus further comprises a catheter assembly including a catheter slidably mounted within the needle lumen. The catheter typically includes a distal port, a proximal connector, and at least one arm extending distally from the proximal connector. The catheter is typically retracted proximally within the needle in an initial configuration of the catheter insertion apparatus. The apparatus usually further comprises an axially compressed coil spring disposed coaxially over a proximal portion of the needle. The coil spring has a distal end engaging an interior surface of the longitudinal passage of the housing and a proximal end engaging a distal face of the proximal hub of the needle when the insertion apparatus is in its initial configuration. A locking disc is configured to hold the coil spring in its axially compressed configuration. Usually, the locking disc is further configured to be engaged by the at least one arm of the catheter assembly when the catheter assembly is distally advanced relative to the housing. Typically, rotation of the catheter assembly after it has been fully advanced will release the locking disc, thus allowing the spring to axially expand to retract the needle. In particular instances of the catheter insertion apparatus of the present invention, prior to rotation of the catheter assembly, the locking disc engages one or more retaining features on an interior surface of the longitudinal passage. In such instances, rotation of the catheter assembly causes the locking disc to rotate and disengage from the one or more retaining feature, thus allowing the coil spring to expand and proximally retract the needle assembly.

In still further particular embodiments, a distal end of the at least one arm of the catheter assembly may have a slot which locks with the retaining feature on the interior surface of the longitudinal passage after the catheter assembly has been rotated. Thus, in a single motion of rotating the catheter assembly, the catheter assembly both locks to the retaining feature and releases the needle so that the needle is automatically retracted by expansion of the spring.

In other specific aspects of the catheter insertion apparatus, once the needle has been fully retracted within the housing and the catheter fully advanced from the housing, the integrated apparatus may be taped to the patient and connected to any conventional fluid or other medicament source. There is no need to detach the needle, and the needle is fully protected and locked within the housing, thus presenting no safety issues.

In still further aspects of the present invention, a method is provided for inserting a catheter into a vein of a patient. A needle on a housing is manually advanced into the vein, where the needle and the housing carry a retracted catheter. The catheter is then manually advanced from the needle into the vein, and the needle is retracted over the catheter into the housing while the catheter remains in the vein. Once the needle is within the housing, the housing may be secured to skin of the patient and is available for connection to a conventional fluid delivery or other medicament system.

In particular aspects of the method, the needle remains fully retracted within the housing when the housing is secured to the skin of the patient. The needle may be retracted manually, e.g. where the user retracts the slider on the housing. Alternatively, the needle may be retracted automatically, e.g. by releasing a constrained spring to axially translate the needle relative to the catheter and the housing.

In still other embodiments, automatic needle retraction can be affected by mechanically coupling the catheter assembly to the needle, thus accomplishing "automatic" needle retraction while eliminating the need for a spring. For example, a pulley assembly can be provided by attaching a pulling end of one or more tethers to the needle and a driving end of each tether to the catheter, The tether will be passed over a "pulley" feature on the body so that the pulling end of the tethers travels proximally to draw the needle proximally into the housing as the driving ends of the tethers are translated distally as the catheter is pushed forward.

In still other instances, an elastic band or other element may be attached to the needle and the housing and loaded under tension. The tensioned element may then be automatically or manually released to drive the needle proximally into the housing.

In a third exemplary embodiment of the present invention, an integrated catheter comprises, and in preferred instances consists of, a housing, a needle cannula, a venous access catheter, and a spring configured to automatically retract the needle after the venous access catheter has been advanced through the needle.

In particular, the catheter insertion apparatus may comprise or consist of a housing having a longitudinal passage and a cannula or other needle assembly slidably mounted within the longitudinal passage of the housing. The longitudinal passage typically extends from a proximal extension to a distal end of the housing, and the needle cannula extends from a proximal hub to a tissue-penetrating distal tip. In an initial configuration, the needle cannula extends distally from the distal end of the housing, fully exposing the tissue-penetrating distal tip to allow percutaneous introduction to a patient's venous lumen.

The venous access catheter is typically formed as an assembly including a catheter body or shaft having a distal port and being slidably mounted within the needle lumen, a proximal connector, and at least one arm extending distally from the proximal connector. The catheter shaft is proximally disposed (retracted) within the needle lumen when the catheter insertion apparatus is in its initial configuration. The spring typically comprises an axially compressed coil spring disposed coaxially over the proximal hub or other portion of the needle cannula, where a distal end of the spring engages an interior surface of the longitudinal passage of the housing and a proximal end of the spring engages a distal face of the proximal hub of the needle when the catheter insertion apparatus is in its initial configuration. A latch on the needle hub engages a locking feature on an inner surface of the longitudinal passage of the housing to hold the needle in place against the force of the compressed spring, wherein the at least one arm of the catheter assembly is configured to disengage the latch from the locking feature after the catheter is distally advanced to allow the spring to decompress and retract the needle into the housing.

In specific instances of the third embodiment of the catheter insertion apparatus, the needle assembly may comprise a needle hub having at least one spring-loaded latch which engages the locking feature on the inside surface of the longitudinal passage in the housing to hold the needle in place where the at least one arm engages and releases the at least one spring-loaded latch from the locking feature as the catheter is advanced. The at least one spring-loaded latch may comprise a cantilevered hook on the needle hub, and the locking feature may comprise an undercut or other slot formed on the inside surface of the longitudinal passage in the housing. The proximal connector of the catheter typically comprises a female luer taper and the proximal extension of the housing typically comprises male luer threads, wherein the female luer taper and the male luer threads are joined to form a complete luer fitting when the catheter is fully advanced through the housing. In most instances, the housing is configured to be taped to a patient after the needle has been retracted.

In a further aspect, the present invention provides a catheter insertion system which includes both a catheter insertion device and a catheter to be inserted into a patient's venous system using the catheter insertion device. The catheter insertion device comprises a housing extending along a longitudinal axis and a needle extending distally, usually coaxially, from a distal end of the housing. The needle will have a longitudinal passage which is coaxially aligned with the longitudinal axis of the housing. The catheter has a length and is sized and shaped to be advanced from a retracted position within the longitudinal passage of the needle to an extended position when at least a portion, typically one-half or more, of the catheter length extends beyond a distal tip of the needle.

In particular aspects of the present invention, the catheter has a distal port configured to direct an outlet flow in a lateral direction (relative to the axial direction of the needle). The distal port has a fixed rotational orientation relative to the longitudinal axis of the housing. In this way, a user can readily control a rotational orientation of the distal port of the catheter as the catheter is being advanced from the needle. Usually, the user will rotationally orient the catheter insertion device which carries the catheter so that the distal port on the catheter is deployed in a desired rotational orientation in the venous lumen. Typically, the distal region of the catheter will be advanced against a wall of the venous lumen and the distal port will be oriented to direct fluid flow from the distal port toward the center of the venous lumen. Such orientation is advantageous as it promotes mixing of the fluid with the blood flow.

In further embodiments of the present invention, the housing of the catheter insertion device may have an upper side and the outflow from the distal port of the catheter may be aligned in a direction toward the upper side of the housing. This allows a user to easily control the direction of the distal port since it will always be aligned with the upper side of the housing which remains visible at all times during catheter deployment.

In other particular embodiments of the present invention, the port may be configured to orient the outlet flow at an angle in a range from 30° to 75° relatively to a longitudinal access of the catheter near its distal end.

In other specific aspects, the catheter may have an atraumatic tip, such as a bullet tip and the outlet port may be formed by a chamfer angled on one side of the bullet tip.

In still other particular embodiments of the present invention, the catheter may have an advancer (typically on a proximal hub) which is disposed through a channel in the upper side of the housing so that the advancer is aligned with the outlet flow of the distal port. The needle may be retractable into the housing so that the housing may be secured to a patient without removing the needle. Alternatively, the housing and the needle may both be "splittable" to facilitate removal of the housing and needle from the catheter after the catheter has been introduced into a vein, as described in US2019/0076628, commonly assigned with the present application, the full disclosure of which is incorporated herein by reference.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The invention will be understood from the following description of preferred embodiments, taken in conjunction with the accompanying drawings, wherein:

FIGS. 6A-6C illustrate use of the catheter insertion tools of FIGS. 1 and 2 for delivering a venous catheter into a venous lumen.

FIGS. 8A-8C illustrate the integrated catheter insertion apparatus of FIG. 7 showing the steps in deploying a catheter and retracting a needle in accordance with the principles of the methods of the present invention.

FIGS. 11A-11C illustrate the steps of the methods of the present invention for advancing the venous access catheter and retracting the venous access needle in accordance with the methods of the present invention.

FIG. 15 is a perspective view of a housing of the integrated catheter insertion apparatus of FIGS. 13A and 13B.

FIGS. 15A and 15B are detailed views of a partial luer fitting incorporated into a proximal end of the housing of FIG. 15 shown in full view and cross-sectional view, respectively.

FIG. 16 is a perspective view of a cannula of the integrated catheter insertion apparatus of FIGS. 13A and 13B.

FIGS. 16A-16C are detailed views of a hub disposed at a proximal end of the cannula illustrated in FIG. 16.

DETAILED DESCRIPTION OF THE INVENTION

Figure 1:
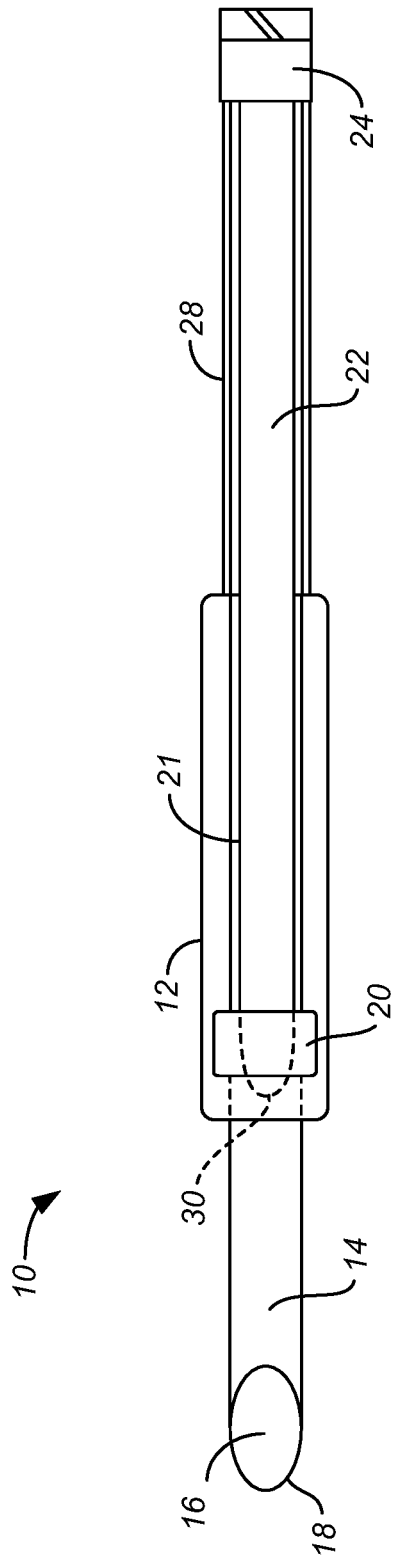
FIG. 1 is a perspective view of a top view of a catheter insertion device constructed in accordance with the principles of the present invention.

The illustrations presented herein are not actual views of any particular catheter insertion device but are merely idealized representations employed to describe example embodiments of the present disclosure. The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. Also note, any drawings accompanying the application are for illustrative purposes only and are thus not drawn to scale. Additionally, elements common between figures may have corresponding numerical designations.

As used herein, the terms "comprising," "including," and grammatical equivalents thereof are inclusive or open-ended terms that do not exclude additional, un-recited elements or method steps, but also include the more restrictive terms "consisting of," "consisting essentially of," and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "below," "lower," "bottom," "above," "upper," "top," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures. For example, the spatially relative terms may refer to a catheter insertion device when the device is disposed on a horizontal surface (e.g., the position depicted in FIG. 1).

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "vascular catheter" means and includes any catheter that may be used for providing access to the vasculature, such as one or more veins or one or more arteries of a patient, such as a midline catheter, a basilic catheter, a cephalic catheter, a centesis catheter (for deployment in the thoracic or abdominal regions of a patient), or another type of catheter. Vascular catheters described herein may comprise an arterial catheter or a venous catheter.

Figure 2:
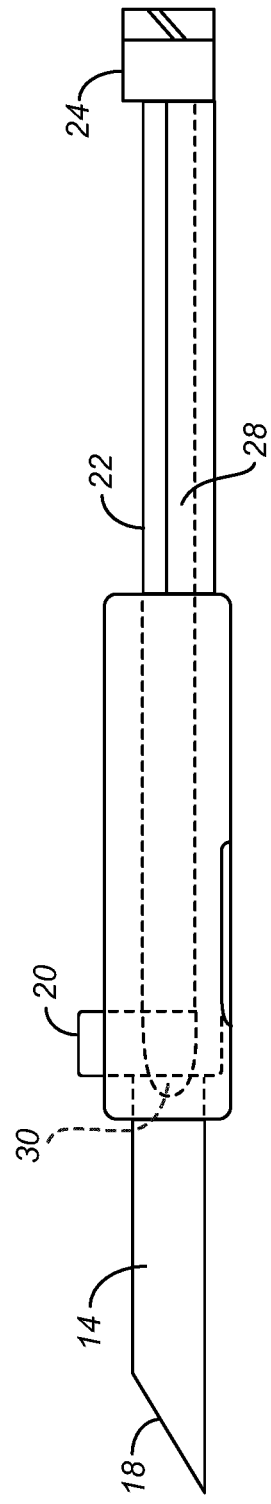
FIG. 2 is a side view of the catheter insertion device of FIG. 1.

Referring to FIGS. 1 and 2, a catheter insertion tool 10 comprises a housing 12 and a needle 14. The needle has a sharp distal tip 16 to allow transcutaneous insertion through a patient's skin into a vessel lumen, such as a venous lumen. The sharp distal tip 16 defines an opening 18 at the distal end of a needle lumen through which a catheter will be introduced into the venous or other vessel lumen, as will be described in more detail below.

A slider 20 is slidably mounted on a surface of the housing 12. The slider 20 is coupled at or near a proximal end of the needle 14 to allow a user to manually retract the needle into an interior space within the housing, as will be described further below. Typically, the slider 20 will be connected through an axial slot 21 or other feature formed in the surface of the housing 12.

A catheter 22 is slidably mounted within the housing 12. Catheter 22 will have a proximal housing 24, typically being or including a luer connector, and a distal tip 30, typically a bullet tip as described in more detail elsewhere herein. Catheter 22 is free to move within the housing 12 and the needle 14 so that it may be manually advanced by pushing on the catheter, typically pushing in a proximal direction on the proximal housing 24. To prevent such movement during needle insertion, however, a locking sheath 28 is provided around a proximal portion of the catheter 22. So long as the locking sheath 28 is in place, as illustrated in FIGS. 1 and 2, the distal tip 30 of the catheter cannot be advanced further into the needle than as shown in broken line.

Figure 3:
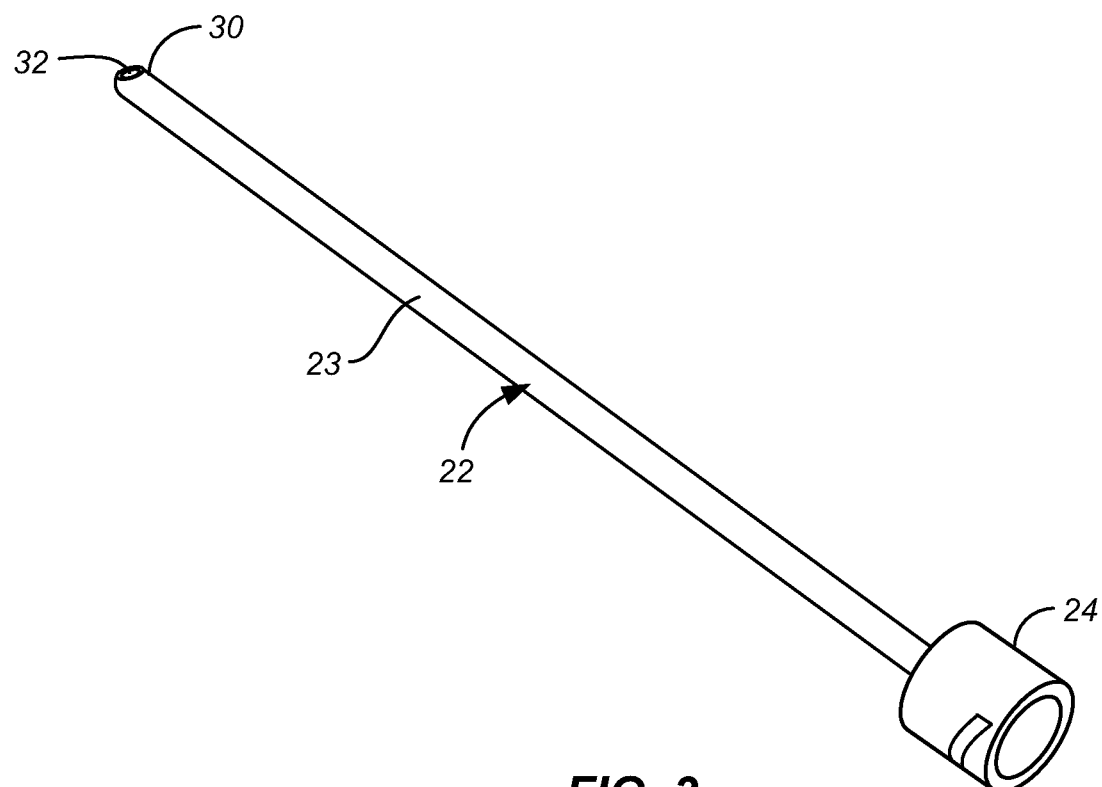
FIG. 3 illustrates a venous catheter having an atraumatic distal tip with a laterally offset outlet port that may be delivered using the catheter insertion tools of the present invention.
Figure 4:
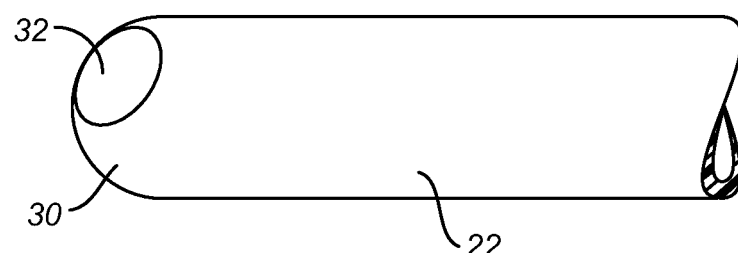
FIG. 4 is a detailed view of the distal end of the venous catheter of FIG. 3.
Figure 5:
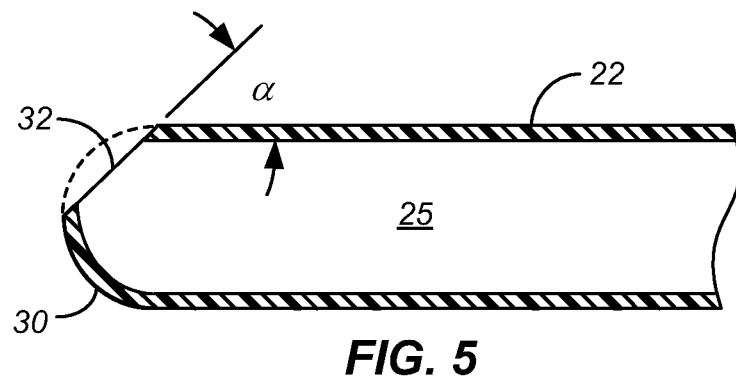
FIG. 5 is a detailed view of the distal end of the venous catheter of FIG. 5, shown in cross-section.

Referring now to FIGS. 3, 4, and 5, a bullet-nosed catheter 22 includes a flexible shaft 23 having a bullet-shaped distal tip 30 (e.g. having a hemispherical distal end) and a proximal housing 24, typically a luer fitting. As best seen in FIGS. 4 and 5, a distal outlet port 32 is formed in the bullet-shaped distal tip 30 of the catheter shaft 23 and is oriented at an angle relative to a longitudinal access of the shaft lumen 25. In the illustrated embodiment, the distal outlet port 32 is formed by cutting or "chamfering" a portion of the bullet-shaped distal tip 30 of the catheter shaft. Typically, the chamfer will be formed at an angle α in range from 30° to 75°, as illustrated in FIG. 5. Other laterally offset outlet ports could also be used. It is desirable that only the outlet port be able to direct fluid from the distal outlet port 32 of the catheter shaft 23 at an angle which is laterally offset or deflected from the longitudinal access of the shaft, as described in more detail below. This allows the user to orient the outlet flow of the catheter 22 so that it will be directed across blood flow to promote mixing in the vein.

In exemplary embodiments, the length of the needle 14 be in a range from 1.5 cm to 5 cm, typically being in a range from 2.5 cm to 3.5 cm. The catheter shaft 23 may have a length in the range from 6 cm to 20 cm, typically being from 8 cm to 14 cm. In such embodiments, a distal region of the catheter shaft having a length in the range from 1.5 cm to 6 cm, typically from 2 cm to 4 cm is available to be advanced from the needle and deployed in the patient's vein as described below.

Figure 6A:
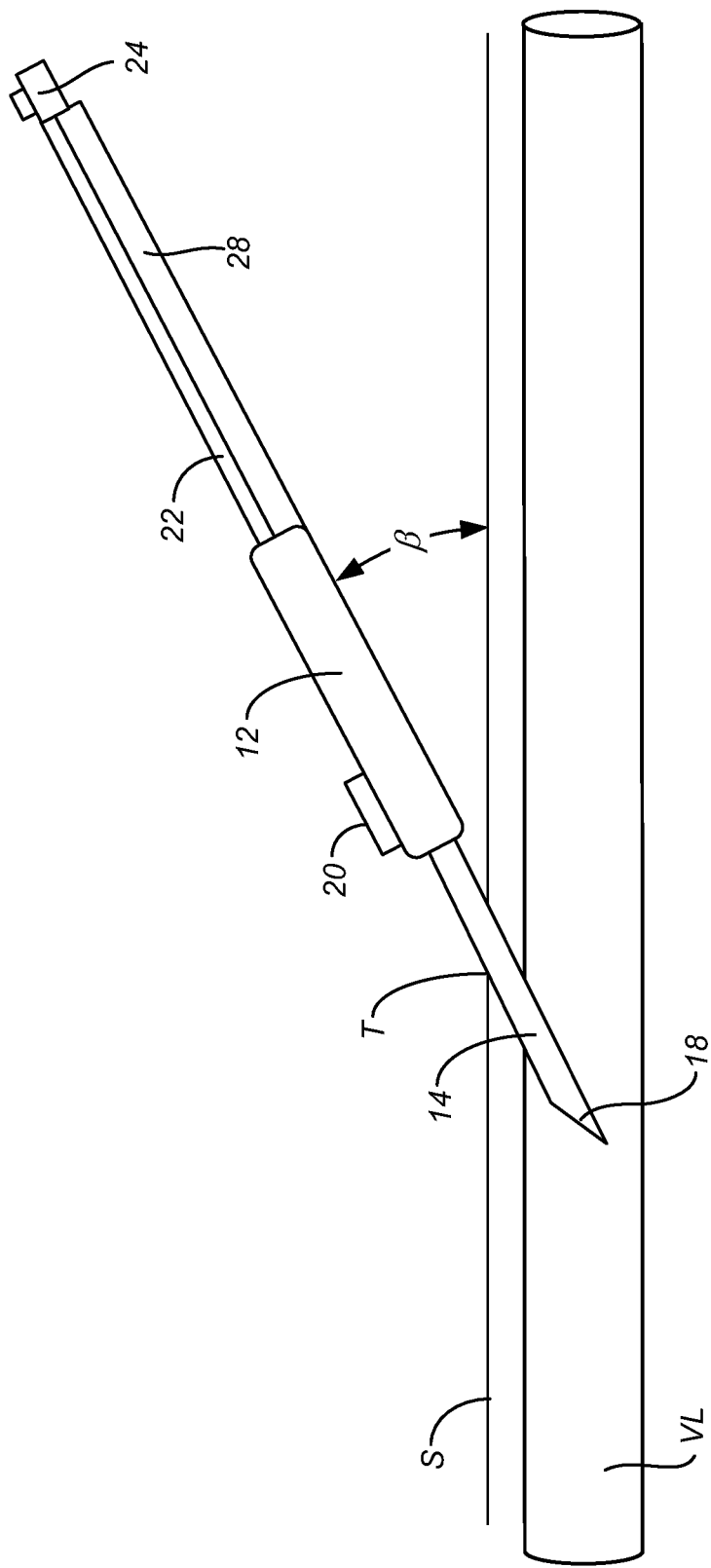

As shown in FIGS. 6A through 6C, the bullet-nose catheter 22 may be deployed in a patient's venous lumen VL by first choosing a target insertion site T on a patient's skin S. A sharp tip 18 on the needle 14 is manually pushed through the skin S at the target site T in a conventional manner so that the tip enters the venous lumen VL and may be positioned generally in the middle of the lumen. The needle will typically be inserted through the skin S at an angle β relative to the venous lumen VL, typically in the range from 30° to 45°, as shown in FIG. 6A.

Referring now to FIG. 6B, once the distal tip 18 of the needle is in place in the venous lumen VL, the locking sheath 28 will be removed from around the catheter 22, allowing a user to manually push the luer connector or other proximal hub 24 or other proximal hub distally so that a distal region of the catheter 22 enters the venous lumen VL. Typically, the proximal hub will be advanced fully so that it engages a proximal end of the housing 12, as shown in FIG. 6B, but in other instances it may be desirable to only partially advance the catheter, resulting in a shorter length of the catheter being within the vessel.

Referring now to FIG. 6C, once the desired length of the catheter has been introduced into the venous lumen VL, the slider 20 will be manually retracted in a proximal direction to proximally retract the needle 14 fully within an interior space of the housing 12. The proximal hub 24, typically a conventional luer connector, is ready to be connected to an external fluid source in the conventional manner. The housing 12 may be taped or otherwise secured to the patient's skin S and the catheter will be considered fully deployed.

Referring now to FIGS. 7 and 8A-8C, a catheter insertion apparatus 100 comprises a housing 102, a cannula 104, typically a needle having a sharpened distal tip 114, and a venous access catheter 106. The catheter is part of a catheter assembly including a proximal connector 108 at a proximal end of the catheter. The proximal connector 108 may be a conventional luer-type fitting having proximal threads 116 of the type which mate with conventional medical fluid delivery systems. The proximal connector 108 will typically also have gripping features 118b which eventually line with gripping features 118a at a proximal end of the housing 102, as shown in FIG. 8C.

Figure 7:
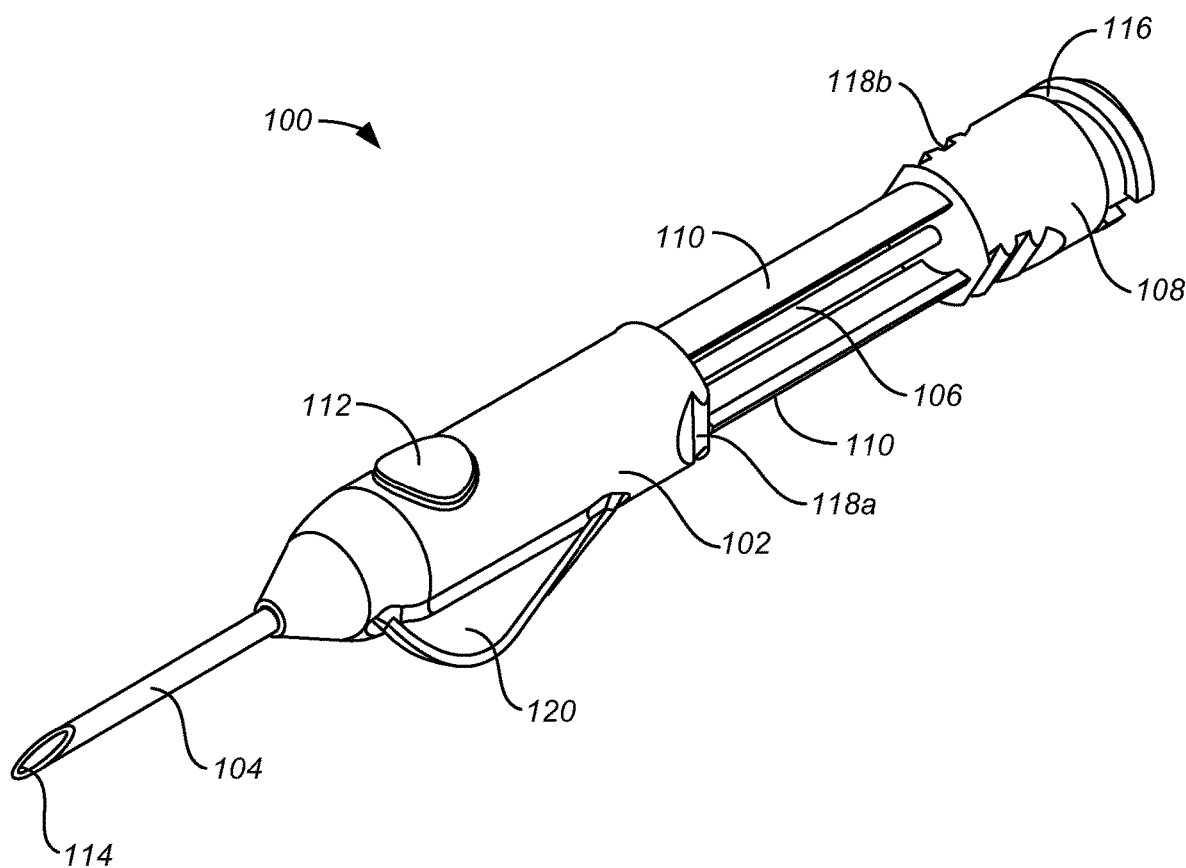
FIG. 7 is a perspective view of an integrated catheter insertion apparatus constructed in accordance with the principles of the present invention.

In an initial configuration (i.e. the configuration used for initial needle penetration into the patient's vein), the catheter 106 will be fully retracted within the needle 104 and the housing 102, as shown in FIGS. 7 and 8A. The proximal connector 108 on the catheter assembly will also be proximally spaced from a proximal end of the housing 102 while being slidably attached to the housing by a pair of arms 110.

The arms 110 serve a number of functions, as described below, but as seen in FIGS. 7 and 8A, will act as rails or guides for advancing the catheter assembly into the interior of the housing 102 as the connector 108 is pushed distally by a user.

The catheter insertion apparatus 100 further includes a flashback window 112 and a pair of taping wings 120 on the housing 102. Flashback window 112 allows the user to detect when blood flows back into the device after the sharpened distal tip 114 first enters a vein, confirming that access has been achieved. The taping wings facilitate taping, wrapping, or otherwise securing the housing to the patient after the catheter 106 has been positioned in the target vein.

After the needle 104 has been introduced into a vein, typically by manual placement in a conventional manner, flashback will be observed through the window 112, and the catheter 106 will be distally advanced from the needle 104 by distally advancing the proximal connector 108, as shown in FIG. 8B. At this point, the catheter 106 will be advanced but the needle 104 will still be in place and the catheter has not yet been locked to the housing. Both retracting the needle 104 and locking the catheter 106 may be achieved by rotating the proximal connector 108 until the gripping features 118a and 118b come into axial alignment, as shown in FIG. 8C. While a number of internal mechanisms are necessary to bring about this change, for the user it is a simple twist of the connector 108 that both retracts the needle and locks the catheter in place.

Figure 9:
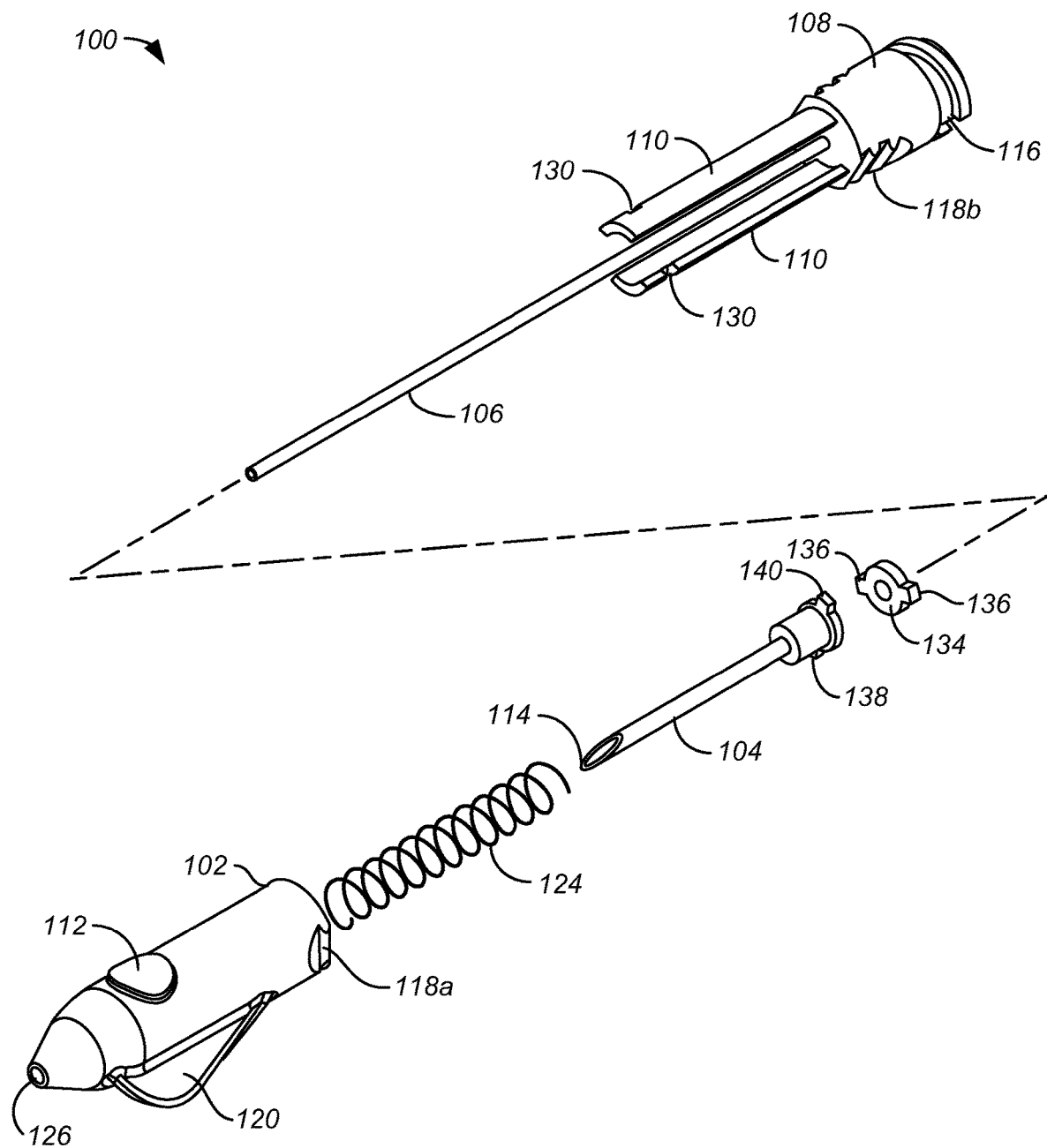
FIG. 9 is an exploded view illustrating the various components of the integrated catheter insertion apparatus of FIG. 7.

Referring now to FIG. 9, the internal components of the catheter insertion apparatus 100 will be identified and described. The needle 104 is aligned to pass through a distal port 126 in the housing 102 and has a needle carriage 138 attached to its proximal end. The needle carriage 138 has a pair of mating wedges 140 (only one of which is visible in FIG. 9) projecting radially outwardly from its proximal end. A locking disc 134 is located on a proximal side on the needle carriage 138 and includes a pair of locking tabs 136. The arms 110 of the catheter assembly each have a locking slot 130 formed near their respective distal ends. A coil spring 124 is disposed between the needle 104 and the housing 102 so that the spring will be compressed between the needle carriage 138 and a proximal surface 103 of an internal passage 105 FIGS. 10A and 10B of the housing 102 when the needle 104 is fully advanced relative to the housing, as described in more detail below.

Figure 10A:
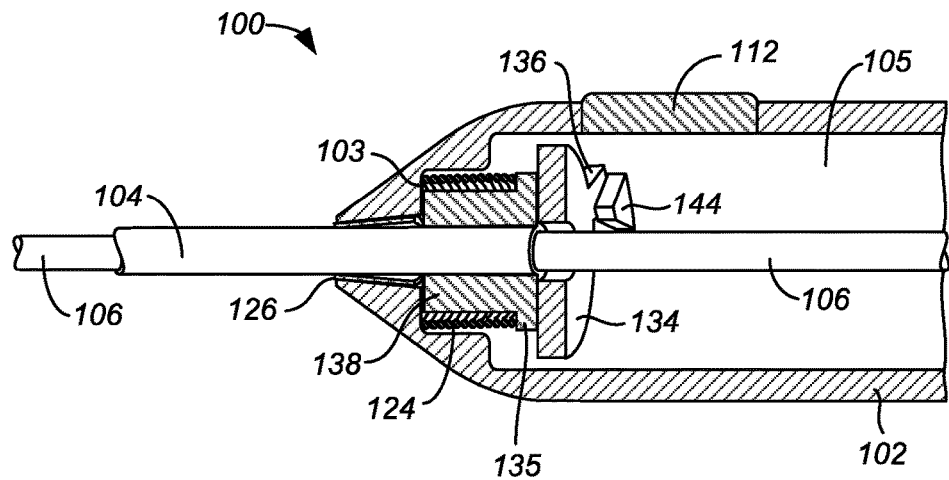
FIGS. 10A and 10B illustrate details of the spring-loaded needle retraction assembly of the present invention.
Figure 10B:
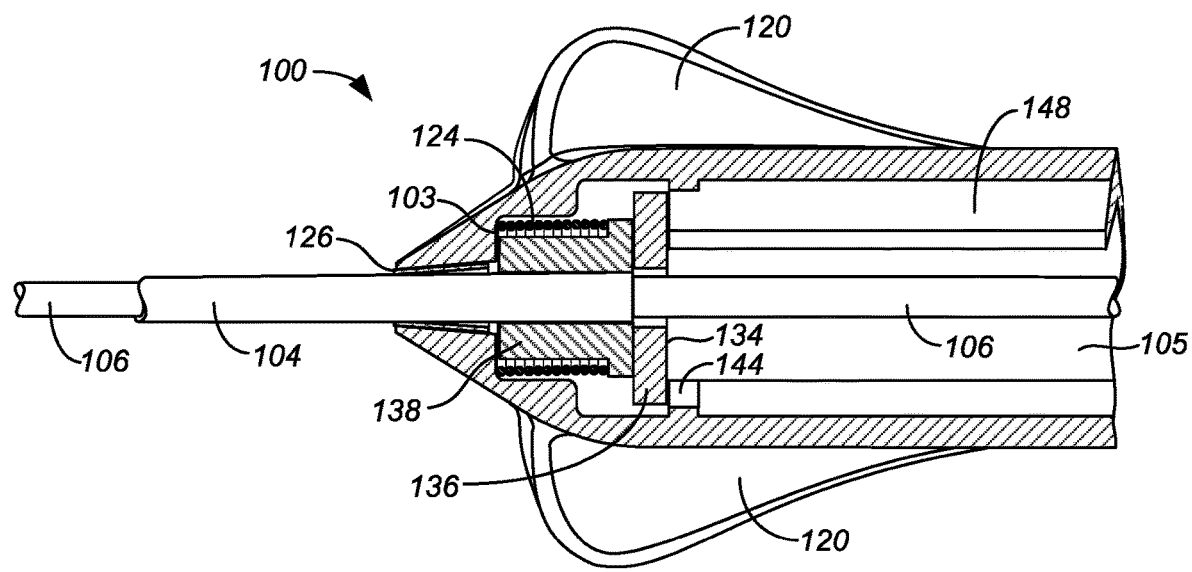

Referring now to FIGS. 10A and 10B, the details of the internal needle retention and release mechanism will be described. In both FIGS. 10A and 10B, the needle 104 is fully extended in the distal direction through the distal port 126 in the housing 102 and held in place by the locking disc 134 which engages and retains the needle carriage 138. Coil spring 124 is fully compressed between a distal surface of a retaining flange 135 at a proximal end of the needle carriage 138 and the proximal surface 103 of the internal passage 105 of the housing 102.

The locking disc 134 is held in place by an engagement between locking tab 136 which extends radially outwardly from the locking disc and a blocking feature 144 formed on an interior surface of the interior passage 105 of the housing 102. Rotation of the locking disc 134 about a longitudinal axis of the housing 102 (perpendicular to a plane of the locking disk) will disengage the locking tab 136 from the blocking feature 144, allowing the disc to translate proximally propelled by expansion of the spring 124, releasing the needle carriage 138 and spring 124. The mechanisms required to rotate the locking disc are described in connection with FIGS. 11A-11C and 12A-12C.

Figure 11A:
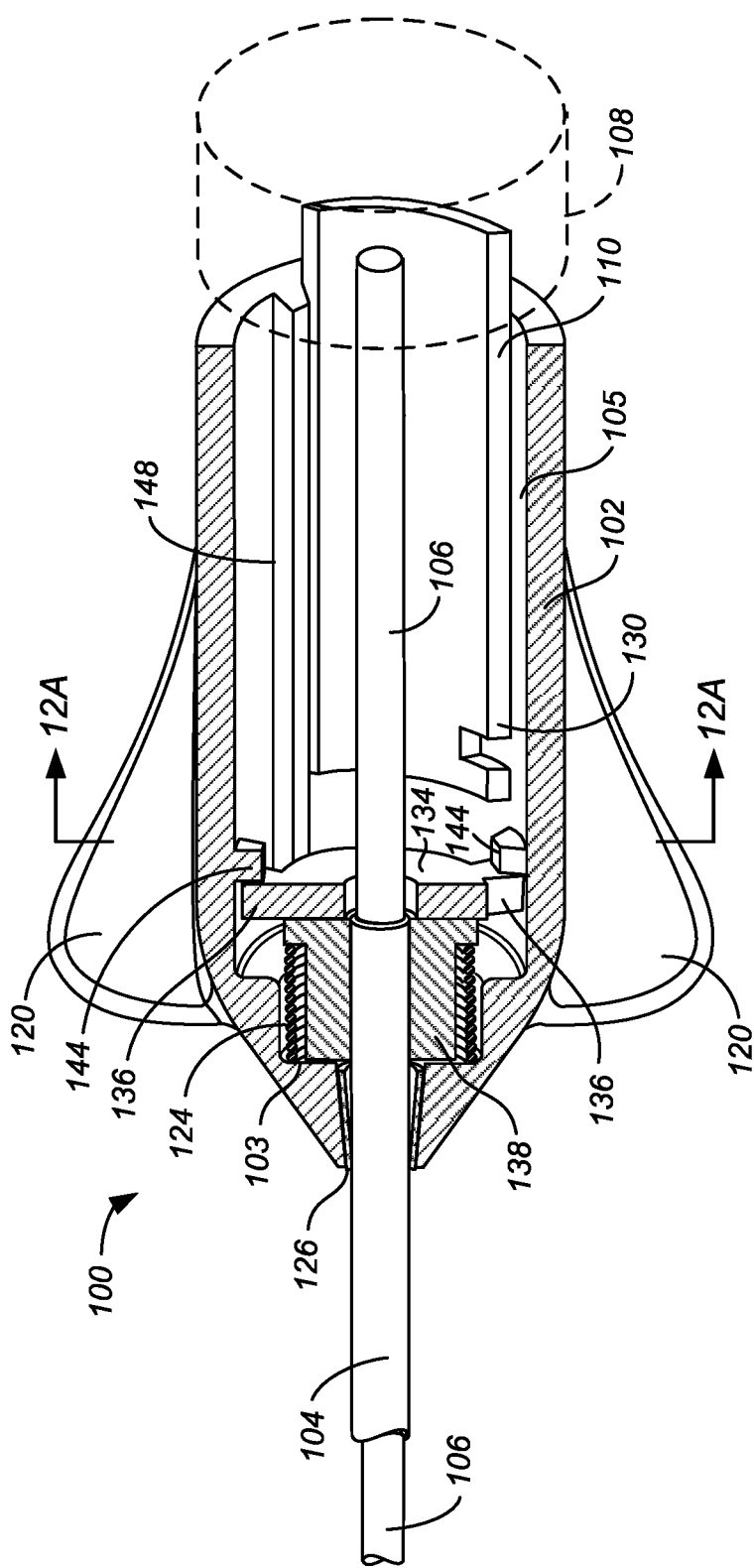

FIGS. 11A illustrate the needle retention and retraction mechanism in the same state as shown in FIGS. 10A and 10B. In addition, FIG. 11A shows one arm 110 of the pair of arms which form part of the catheter assembly shown in FIG. 9. The proximal connector 108 is shown in broken line. All components of the catheter insertion apparatus 100 shown in FIG. 11A are in their initial configuration where the needle is fully advanced through the distal port 126 in the housing 102 and the catheter 106 retracted inside of the needle, as shown in FIGS. 7 and 8A.

Figure 11B:
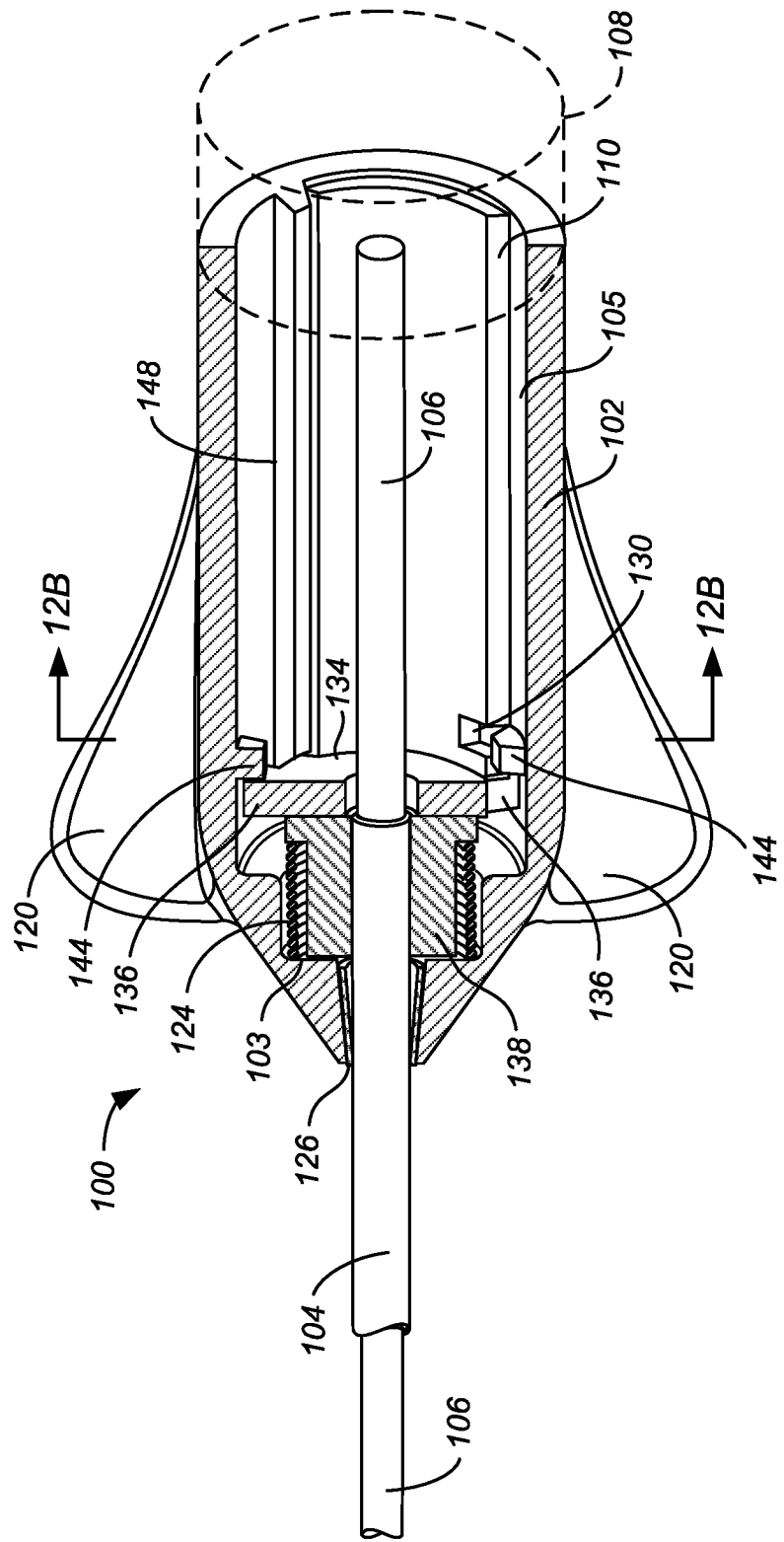

In order to both advance the catheter 106 and release the locking disc 134, the catheter assembly may be distally translated by pushing on the proximal connector 108 to engage a distal surface of the proximal connector against a proximal end of the housing 102, as shown in FIG. 11B. Such axial translation of the connector 108 will fully extend a distal tip of the catheter 106 beyond the sharpened distal tip 114 of the needle 104, as shown in FIG. 8B. At this point, however, as shown in FIG. 11B, the needle 104 remains distally advanced through the distal port 126 in the housing 102 and the catheter 106 is not yet locked in place. In this state, the catheter 106 could be accidentally retracted simply by pulling on the proximal connector 108 and/or pushing on a distal end of the catheter 106 in a proximal direction.

In order to both lock the catheter 106 to the housing 102 and release the locking disc 134 to allow the needle 104 to retract under the force of spring 124, the proximal connector 108 may be rotated to the position shown in FIGS. 8C and 11C. Such rotation causes a distal surface 142 of the arm 110 to engage and rotationally displace the locking tab 136 on the locking disc 134. Such rotation takes the locking tab 136 out of axial alignment with the blocking feature 144. When the locking tab is displaced, the locking disc 134 is free to translate proximally under the force of the spring 124 which is released from compression.

Simultaneously, as the arm 110 rotates, the locking slot 130 on the arm will engage and lock onto the blocking feature 144 on the interior wall of the housing 102, as shown in FIG. 11C. Such engagement and locking prevent further axial translation of the catheter assembly. As a further safety feature, subsequent rotation of the proximal connector 108 is prevented by capturing the locking tab 136 on the locking disc 134 between one side of an alignment rail 148 and an opposing surface of the proximal end of the arm 110, as shown in FIG. 11C. It will be appreciated that the alignment rail 148 acts as a guide for the locking tab as it is proximally translated by the expansion of spring 124, thus assuring that it is positioned between the alignment rail and the arm 110 when the needle is fully retraced and the catheter fully advanced. This safety feature is of a particular advantage as it prevents accidental release of the needle after the housing has been taped to the patient and connected to the fluid delivery system.

Figure 12A:
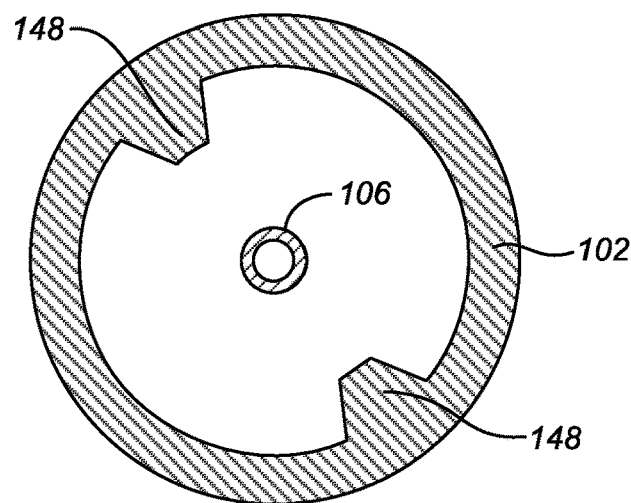
FIGS. 12A-12C are cross-sectional views taken along lines 12A-12A, 12B-12B, and 12C-12C, in FIGS. 11A-11C.
Figure 12B:
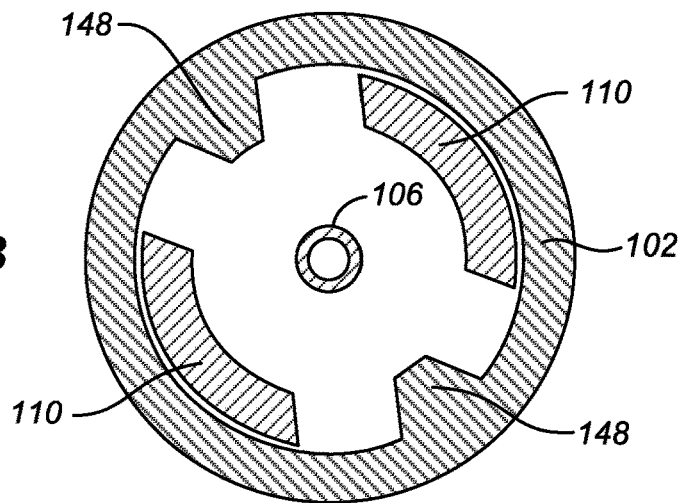
Figure 12C:
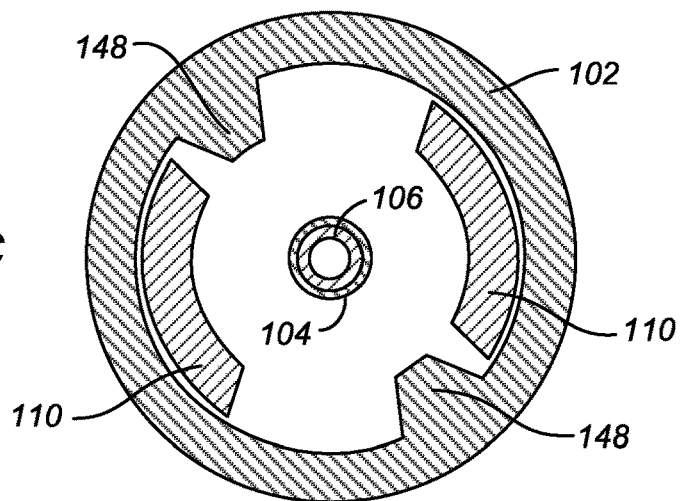

Positioning of the alignment rails 148 and the arms 110 of catheter assembly during various stages of the operation of the catheter insertion apparatus 100 can be observed in FIGS. 12A-12C which are cross-sectional views taken along lines 12A-12A, 12B-12B, and 12C-12C of FIGS. 11A-11C, respectively.

Figure 13A:
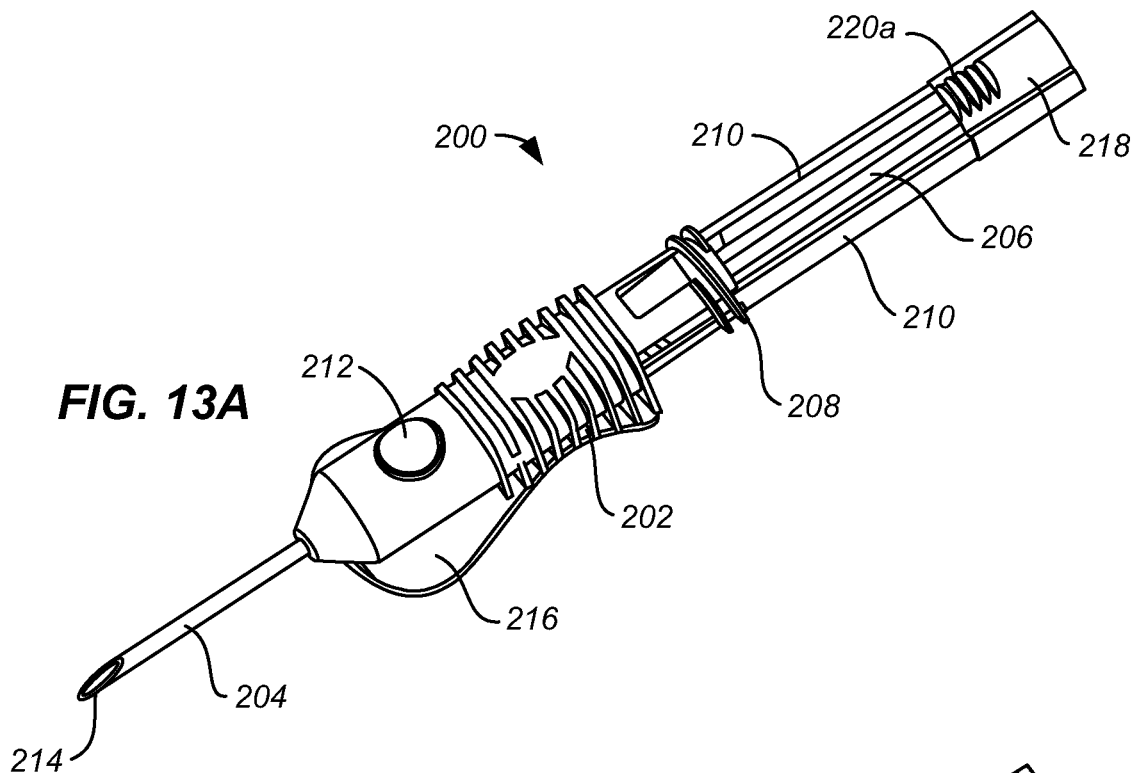
FIGS. 13A and 13B are perspective views of a further embodiment of an integrated catheter insertion apparatus constructed in accordance with the principles of the present invention shown in full view and cross-sectional view, respectively.
Figure 13B:
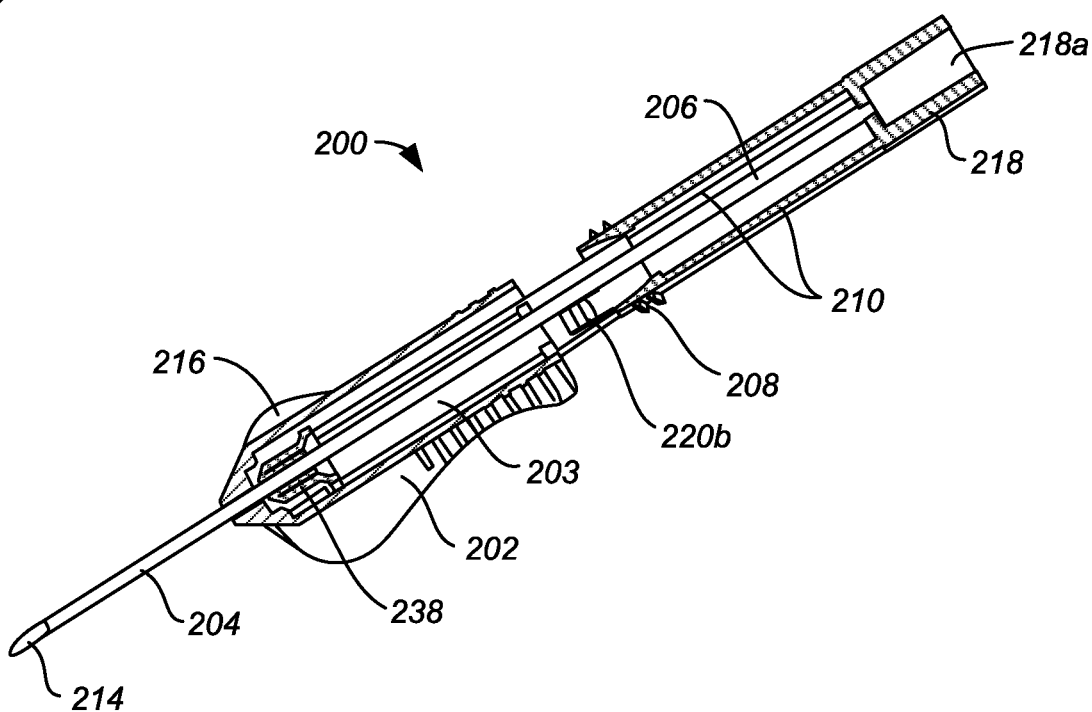

Referring now to FIGS. 13A and 13B, a catheter insertion and attachment apparatus 200 according to a third embodiment of the present invention comprises a housing 202, a needle cannula 204, such as a hypotube needle or similar injection device having a sharpened distal tip 214, and a venous access catheter 206. The venous access catheter 206 is received in an axial passage 203 (FIG. 13B) within the housing 202 and has a partial (inner) luer fitting 218 at its proximal end. A pair of arms 210 is attached to the partial luer fitting 218 and extend from the fitting in a distal direction parallel to a longitudinal axis of the venous access catheter 206. A distal end of each arm 210 terminates in wedge tip 228 which is configured to release the needle cannula 204 from temporary attachment to the housing 202 as the catheter 206 is distally advanced within the passage 203 of the housing 202. A second partial (outer) luer fitting 208 is formed on a proximal extension 234 at a proximal end of the housing 202. The second partial luer fitting includes external luer threads 208a which form the attachment portion of the luer when external tubing is attached to the catheter. In particular the luer becomes functional when the inner luer fitting 218 is inserted into the outer luer fitting 208 as will be described in greater detail below. Typically, the housing 202 will include a pair of taping wings 216 to facilitate securing the housing 202 to the patient's skin after catheter insertion and needle retraction.

As further shown in FIGS. 13A and 13B, in the initial configuration of the catheter insertion and attachment apparatus 200, the needle cannula 204 is fully extended in a distal direction from the housing 202 and the access catheter 206 is fully retracted in a proximal direction within the housing 202. In this configuration, the cannula needle 204 is ready to be percutaneously inserted into a patient's vein. The sharpened the distal tip 214 is inserted into a lumen of a target vein, and entry is confirmed by observing flashback in a window 212 formed in a wall of the housing 202. A complete description of needle insertion, catheter advancement, needle retraction, and external tubing connection is made with reference to FIGS. 19A-19C and FIGS. 20A-20C below.

Figure 14:
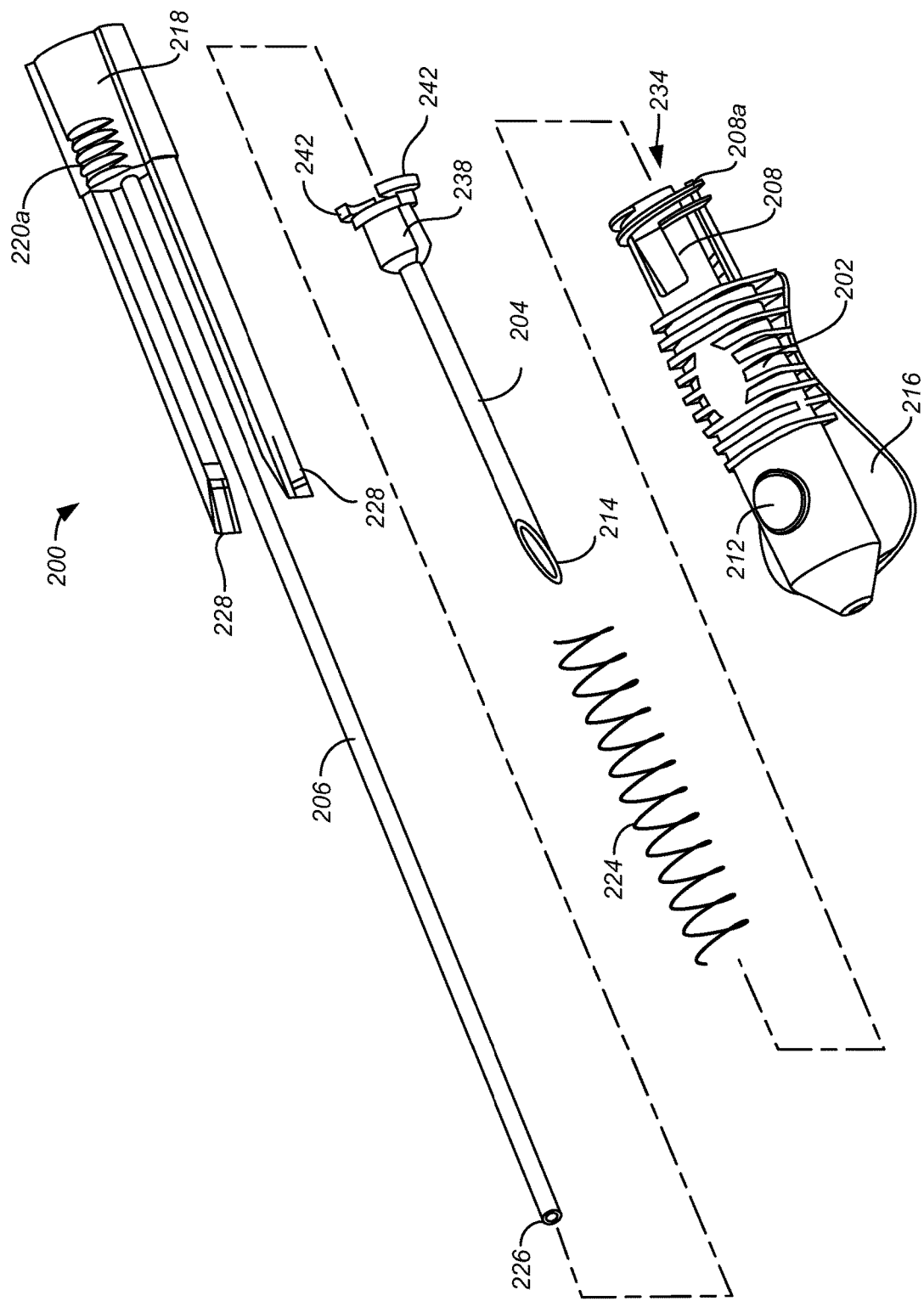
FIG. 14 is an exploded view illustrating the various components of the integrated catheter insertion apparatus of FIGS. 13A and 13B.

Referring now to FIG. 14, each component of the catheter insertion and attachment apparatus 200 is illustrated in isolation. The catheter insertion and advancement apparatus 200 will typically consist of only four components. In addition to the housing 202, needle cannula 204, and venous access catheter 206 described previously, the apparatus 200 will usually include only a coil or other compression spring 224. It is a particular advantage of this embodiment of the present invention that only four separate components are necessary, substantially simplifying fabrication and assembly of the complete product. As best seen in FIG. 14, the partial luer fitting 218 on the access catheter 206 includes a plurality of locking or retention teeth 220a formed on its outer surface. As seen in FIG. 13B, a plurality of locking or retention teeth 220b are also formed on an inner surface of the proximal extension 234 of the housing 202. When the catheter 206 is fully advanced into the housing 202, the locking teeth 220a on the partial luer fitting 218 will engage the locking teeth 220b on the proximal extension of the housing. In this way the teeth 220a and 220b, which are formed as interlocking ratchets, will engage each other and lock or affix the catheter to the housing to prevent accidental retraction. The venous access catheter 206 further includes a distal catheter port 226. The distal catheter port 226 may take any conventional form but will typically have an upward configuration similar to that describe previously.

As further seen in FIG. 14, the needle cannula 204 has a hub 238 and its proximal end opposite the sharpened distal tip 214 formed at the distal end. The needle hub 238 has a pair of engagement hooks or tangs 242 which serve to "releasably" lock the needle cannula in the distally forward configuration prior to retraction of the needle after the catheter has been advanced, as will be described in greater detail below.

Figure 18:
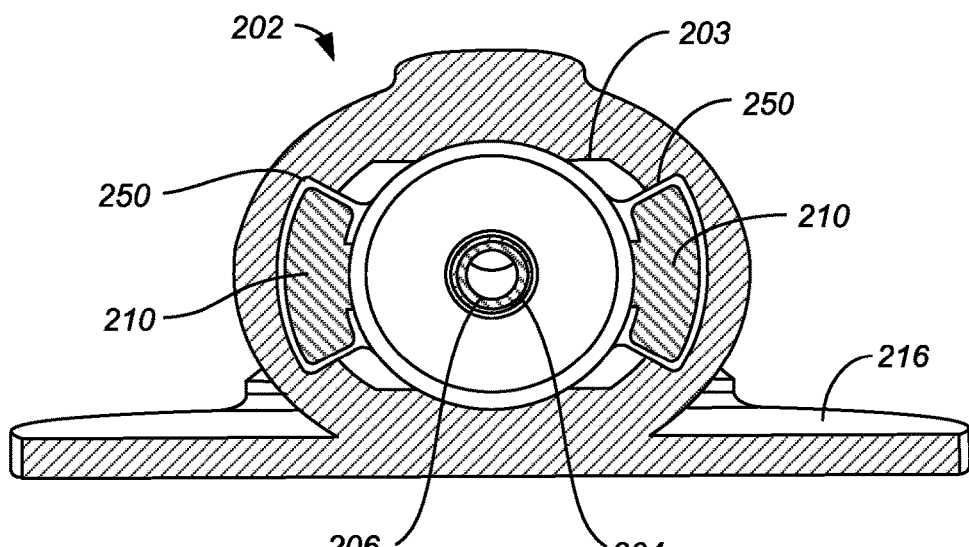
FIG. 18 is a cross-sectional view of the housing illustrating channels formed into an internal wall of the housing which receive two arms of the catheter assembly to allow advancement and alignment of the catheter assembly in the housing.

Referring now to FIGS. 15, 15A, and 15B, the proximal extension 234 of the housing 202 will be described in greater detail. The proximal extension 234 comprises a pair of semi-cylindrical shell elements 232 having a pair of laterally opposed gaps 230 therebetween. The luer threads 208 extend around the semi-cylindrical shell elements 232 and over the gap 230, allowing the wedge tips 228 on the arms 210 of the venous access catheter 206 to be advanced beneath the external threads 208 and through channels 250 on an inner wall of the axial passage 203 of the housing 202, as best seen in FIG. 18. In this way, the wedge tips 228 can be advanced to the needle cannula hub 238 as the catheter 206 is being advanced through the needle cannula 204. When the wedge tips 228 reach the needle cannula hub 238, they will disengage the needle cannula hub from the housing wall, as described in more detail below, allowing the compressed spring 224 to decompress and retract the needle proximally over the venous access catheter 206 and into the axial passage 203 of the housing 202.

Referring now to FIGS. 16 and 16A-16C, the needle cannula assembly 204 will be described in greater detail. The needle cannula assembly 204 includes a conventional needle shaft 204a having a sharpened distal tip 214 at its distal end. The cannula hub 238 is attached to a proximal end of the shaft 204 and comprises a cylindrical wall having a pair of opposed cantilever spring elements 240 formed therein. The cantilever springs are attached to the wall at their distal ends so that the engagement hooks or tangs 242 at their proximal ends maybe resiliently compressed inwardly to release the needle hub from engagement with the housing wall, as will be described below. Each tang or hook 242 has a beveled surface 244 which is configured to be engaged and compressed by the wedge tips 228 of the arms 210 to effect the desired release. As shown in FIG. 16C, the spring coil 224 is maintained in a compressed configuration prior to release of the needle for retraction into the housing. Release of the needle cannula hub 238 from engagement with the housing 202 allows the spring 224 to decompress and drive the needle cannula assembly 204 proximally so that it fully retracts into the housing prior to attachment of external tubing.

Figure 17A:
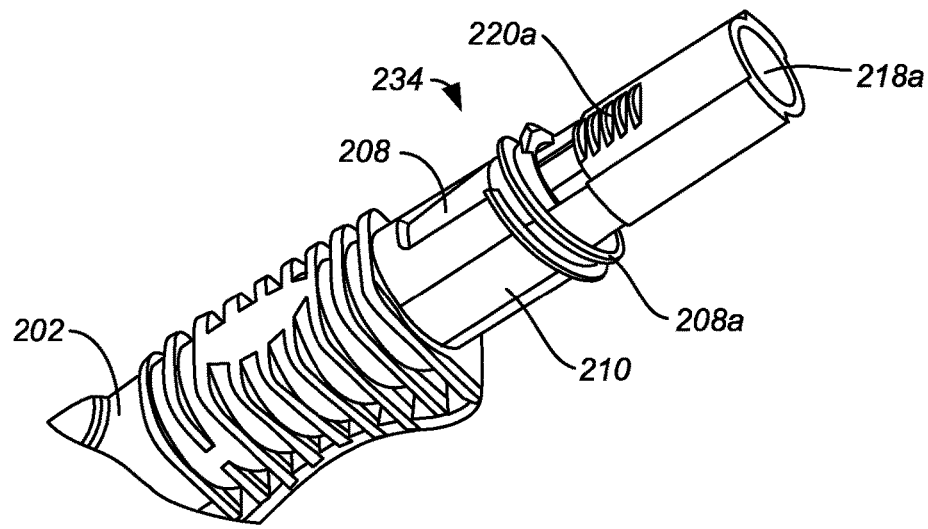
FIGS. 17A and 17B are detailed views illustrating how the partial luer fitting incorporated into the proximal end of the housing of FIG. 15 mates with a partial luer fitting incorporated into a proximal end of a catheter assembly to form a complete luer fitting.
Figure 17B:
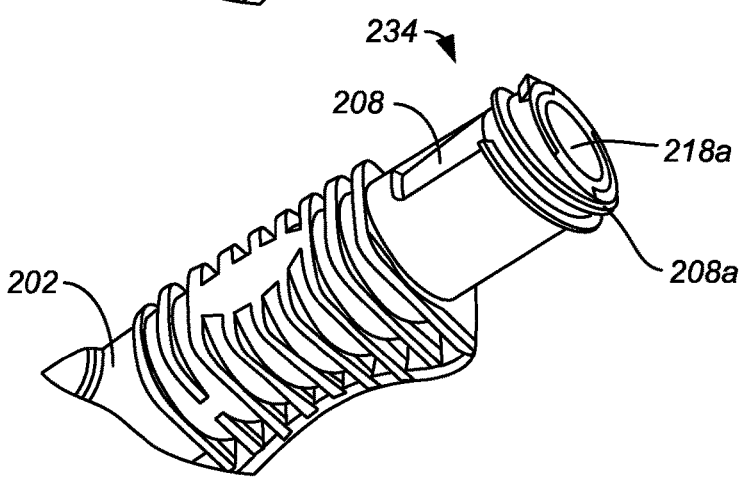

Referring now to FIGS. 17A and 17B, engagement between the partial luer fitting 218 on the venous access catheter 206 with the partial luer fitting 208 on the housing 202 will be described. In FIG. 17A, the partial luer fitting 218 has been advanced to a point where the locking teeth 220a are just about to enter an interior of the proximal extension 234 of the housing 202. It can be seen that arms 210 are entering the housing 202 through the gaps 230 present in the wall of the proximal extension 234. In particular, the arms 210 pass beneath the luer threads 208. Once the partial luer fitting 208 on the catheter 206 is fully advanced into the proximal extension 234, the combination of the partial luer fittings 208 and 218 will form a complete male luer fitting suitable for attachment to a conventional female luer fitting as commonly found on medical tubing. After full insertion of the catheter 206 into the housing 202, the locking teeth 220a on the partial luer fitting 218 will engage the locking teeth 220b (FIG. 15B) on the inner surface of the proximal extension 234. In this way, the catheter will be locked in place within the housing.

FIG. 18 shows a cross-sectional view of the needle cannula 204 and catheter assembly 206 present in the housing 202. In particular, it can be seen that arms 210 are advanced through channels 250 formed on the inner wall of the axial passage 203 within the housing 202. As shown in FIG. 18, the venous access catheter 206 remains within an inner lumen of the needle cannula 204 after the catheter has been advance and the needle catheter retracted.

Figure 19A:
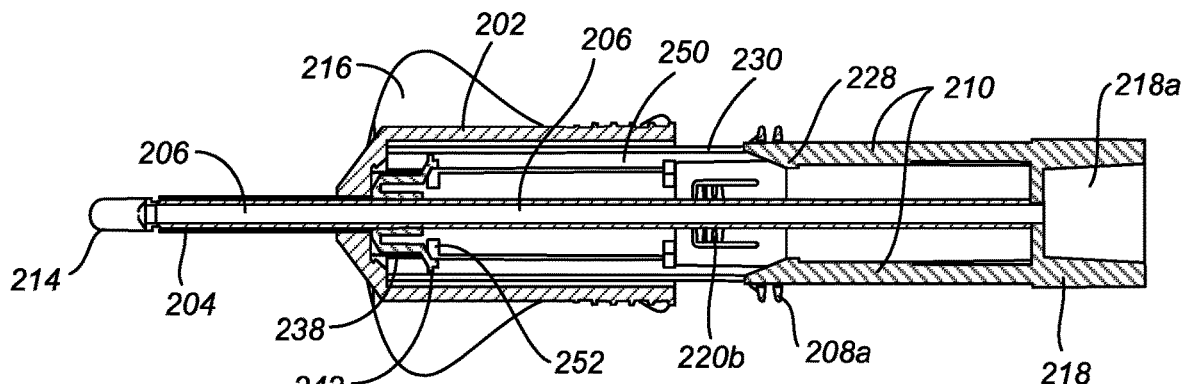
FIGS. 19A-19C illustrate method steps of the present invention for deploying the integrated catheter insertion apparatus of FIGS. 13A and 13B in accordance with the principles of the present invention, shown with the integrated catheter insertion apparatus in a top, cross-sectional view.

Referring now to FIGS. 19A-19C and 20A-20C, stepwise advancement of the catheter assembly 206 in to the housing 202 and retraction of the needle cannula 204 into the housing will be described. As shown in FIG. 19A, the sharpened distal tip 214 of the needle cannula 204 extends fully distally of the housing 202 and is ready for insertion through the patient's skin into the venous lumen. At this point, the catheter assembly 206 is fully retracted in a proximal direction and held in place by engagement of the wedge tips 228 of the arms 210 with the proximal extension 234 of the housing 202. The wedge tips 228 on the distal ends of the arms are initially located beneath the lower threads 208 and are disposed in the gap 230.

Figure 19B:
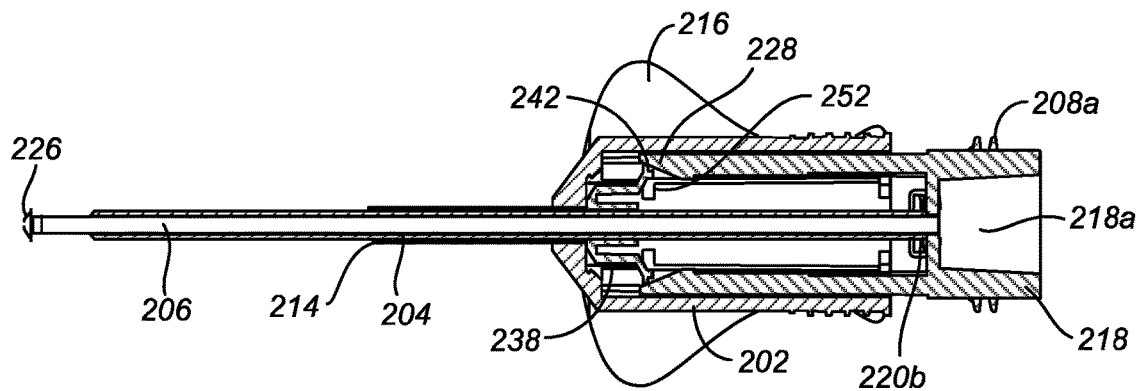
Figure 19C:
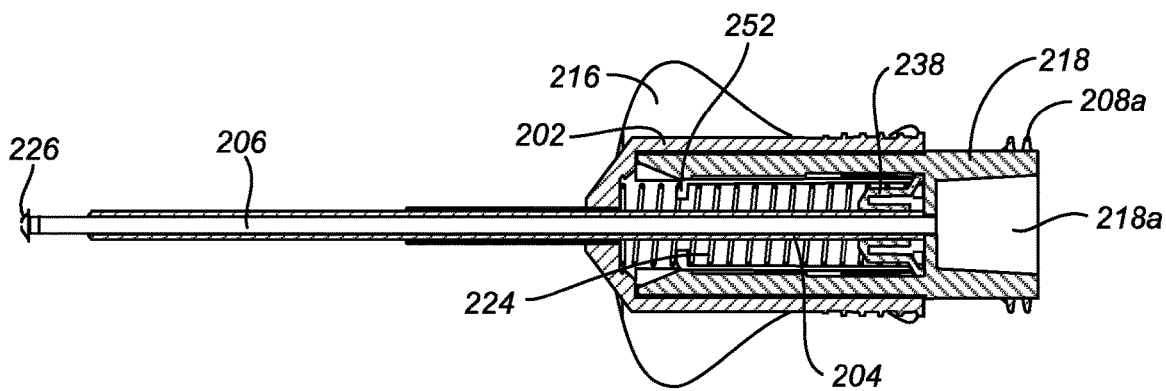
Figure 20A:
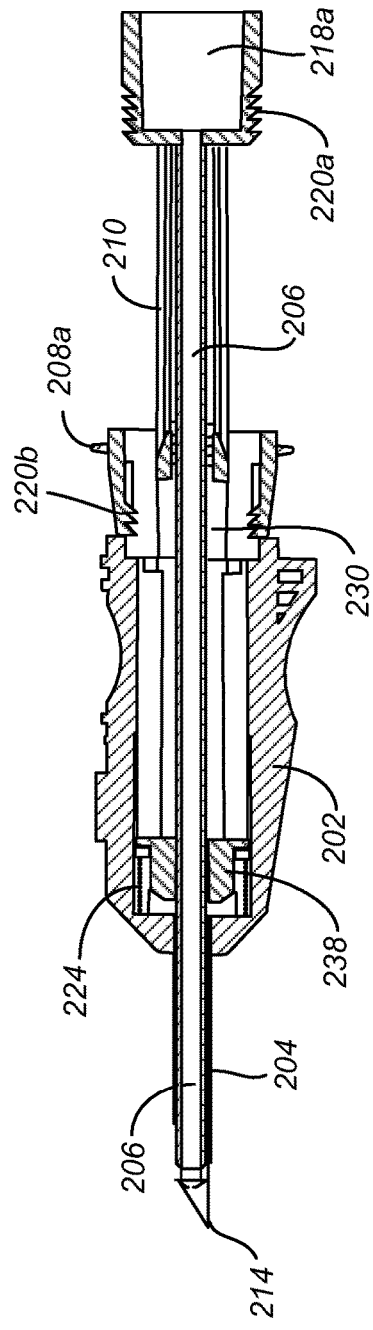
FIGS. 20A-20C illustrate method steps of the present invention for deploying the integrated catheter insertion apparatus of FIGS. 13A and 13B in accordance with the principles of the present invention, shown with the integrated catheter insertion apparatus in a side, cross-sectional view.
Figure 20B:
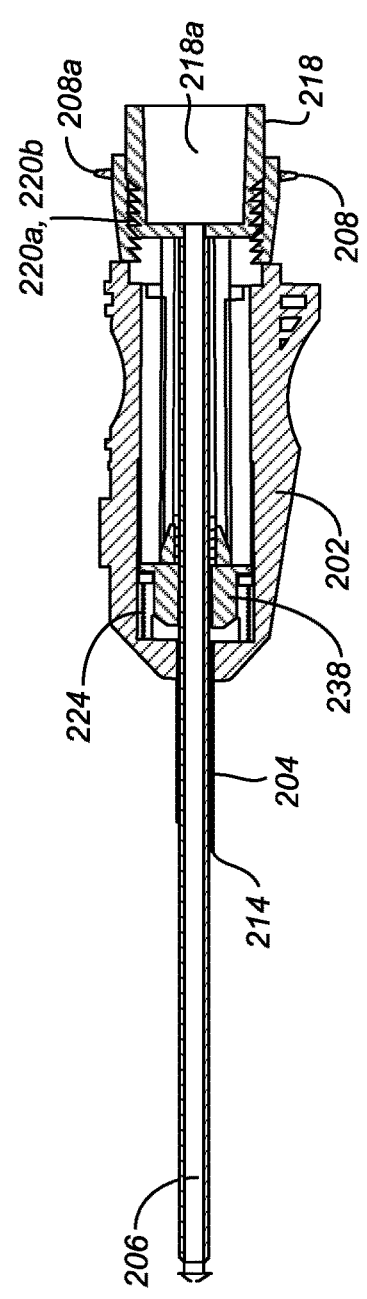
Figure 20C:
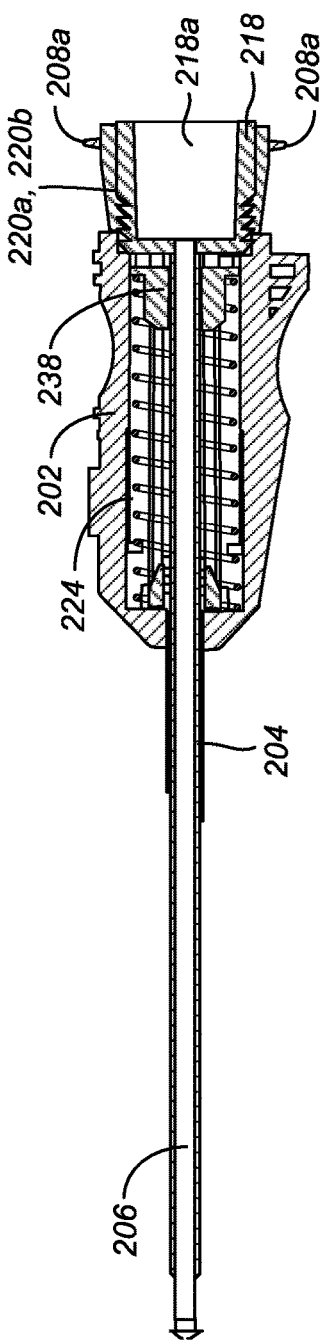

After the needle 204 has been advanced into the venous lumen, the catheter 206 is advanced into the venous lumen by distally pushing the partial luer fitting 218 into the partial luer fitting 208 formed on the proximal extension 234 of the housing, as shown in FIGS. 19B and 20B. The external lower threads 208 are disposed over the exterior of the partial lower fitting 218 in one orientation (FIG. 19B) and are attached to the semi-cylindrical elements of the proximal extension in another orientation (FIG. 20B). As the wedge tips 228 are distally advanced, they engage the engagement hooks or tangs 242 on the needle hub 238. In particular, the inclined surfaces of the wedge tips 228 engage the beveled surfaces 244 (FIGS. 16A and 16B) of the cantilever springs 240 forcing the springs inwardly and disengaging the engagement hooks or tangs 242 from retention slots 252 formed on the inner wall of the axial passage 203 of the housing 202, as best seen in FIG. 19B. Once the engagement hooks 242 are released from the engagement slots 252, the needle hub 238 will be released to translate freely, and the compressed spring 224 will decompress to translate the needle hub 238 proximally, retracting the needle cannula 204 fully into the housing, as shown and FIGS. 19C and 20C.

Figure 21A:
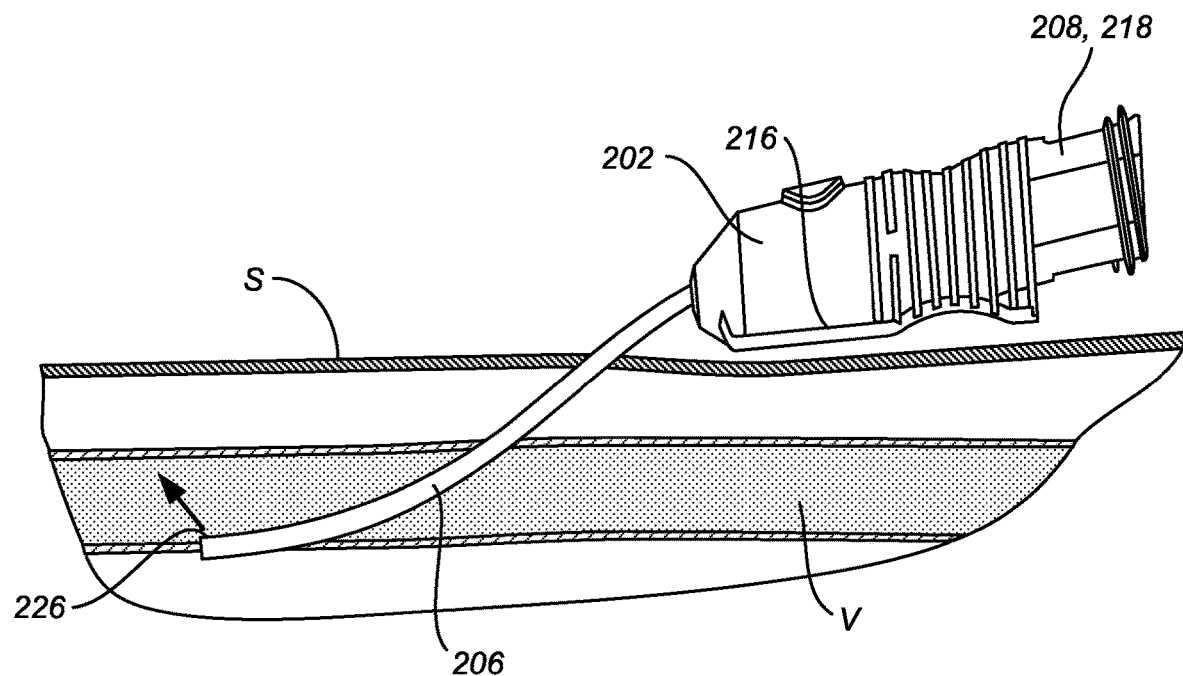
FIGS. 21A and 21B illustrate the integrated catheter insertion apparatus of FIGS. 13A and 13B after the catheter has been introduced into a vein and the cannula retracted into the housing.
Figure 21B:
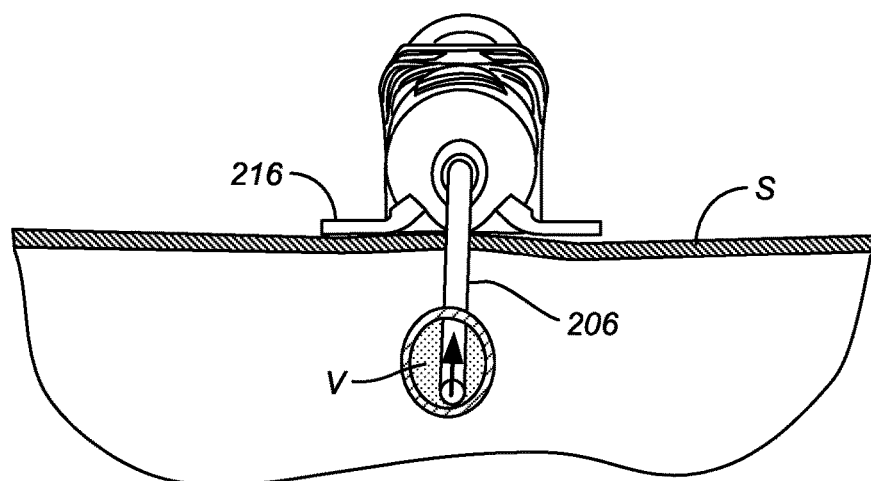

Referring now to FIGS. 21A and 21B, placement of the catheter 206 into the lumen of a vein V is accomplished by advancing the needle percutaneously through the patient's skin S, further advancing the catheter into the vein lumen, and then retracting the needle, as just described. In a preferred embodiment, the distal port 226 of the catheter 206 will be oriented upwardly to provide the advantages described previously in this patent application.

Figure 22A:
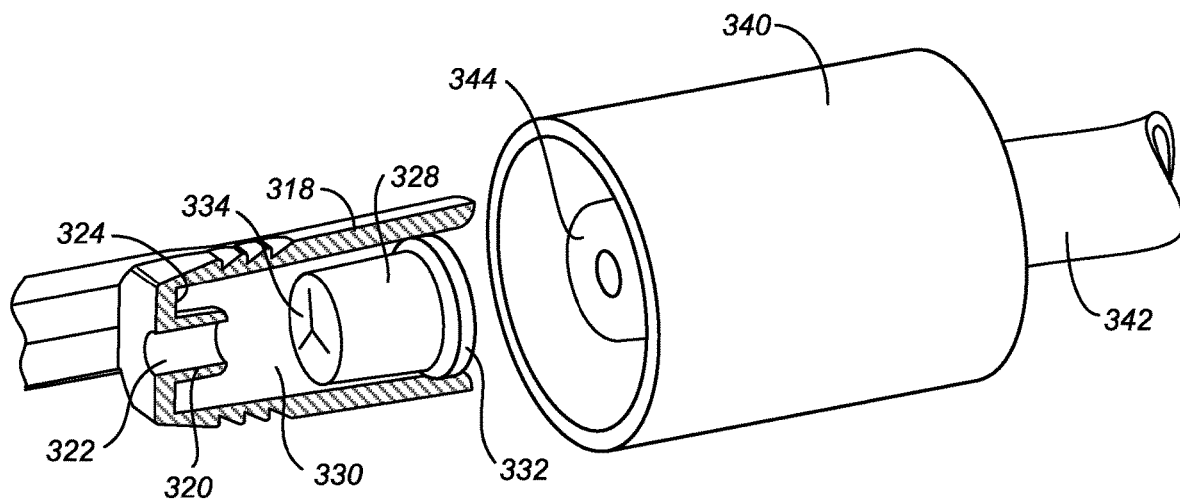
FIGS. 22A-22C illustrate an optional blood control valve disposed in the catheter hub which opens from a proximal, closed configuration (FIG. 22A) to a distal, open confirmation (FIG. 22C) as it is distally advanced in a passage of the hub by attachment of an external luer connector.
Figure 22B:
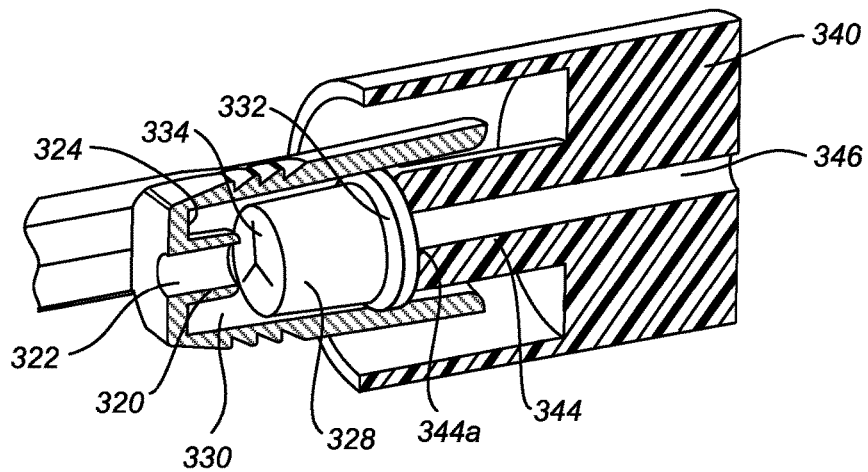
Figure 22C:
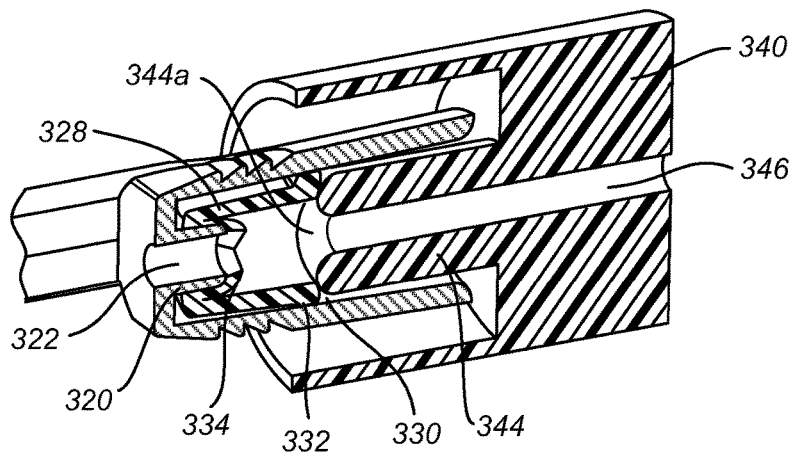

Referring now to FIGS. 22A to 22C, an alternative hub 318 typically formed as an inner luer fitting (shown without an outer luer fitting for simplicity of illustration) may be modified by increasing it length (relative to previously illustrated inner luer fitting 218a) and providing a male post 320 defining a blood outlet port 322 on a distal surface 324 of an interior axial passage 330 thereof. A blood control valve 328 having a split valve element 334 may be translatably disposed in the axial passage 330 of the inner luer fitting 318. The blood control valve 328 is typically formed from a blood-compatible polymer, such as a silicone polymer, and may conveniently have a "top-hat" configuration with a rim 332 formed circumferentially about its proximal end with the split valve element 334 formed in a distal surface thereof. The rim 332 is configured to act as both a seal and a bearing surface that allows the blood control valve 328 to be advanced from a proximal location, as shown in FIG. 22A, to a distal location, as shown in FIG. 22C. As described in more detail below, the split valve element 334 closed as the needle initially penetrates the target vein or other blood vessel to allow blood flashback and gas venting but inhibit blood leakage from the hub. After penetration is confirmed by observing the flashback, an external IV connector 340 or other connector is attached to the inner luer fitting.

The external IV connector 340 is typically attached to a fluid delivery tube 342 which may be connected to a conventional saline or other fluid delivery bag (not shown). As shown in FIG. 22B, the external IV connector 340 has an internal male rod 344, typically molded into the body of the external IV connector 340, having a central lumen 346 which can receive a fluid flow from the tube 342 when such flow has been initiated. As a needle (e.g. needle 204 in FIG. 16) is inserted distally into a target vein or other patient blood vessel, blood will flow proximally through the needle lumen into the hub 318 which will typically be transparent or have a transparent window to allow a user to observe blood "flashback" confirming that the needle has entered the blood vessel. The split valve element 334 of the blood control valve 328 allows gas initially present in the hub 318 to vent while inhibiting blood loss from the hub. To open the valve element to allow infusion, a tip 344a of the male rod 344 engages the rim 332 of the blood control valve 328 to push the split valve element 334 against the male post 320 which forces the split valve element to open, as shown in FIG. 22C. The silicone or other polymeric material of the valve element will be displaced to fit around the male post inside the catheter assembly hub and will remain there for the remainder of the procedure.

While the present invention has been described herein with respect to certain illustrated embodiments, those of ordinary skill in the art will recognize and appreciate that it is not so limited. Rather, many additions, deletions, and modifications to the illustrated embodiments may be made without departing from the scope of the invention as claimed, including legal equivalents thereof. In addition, features from one embodiment may be combined with features of another embodiment while still being encompassed within the scope of the invention as contemplated by the inventors. Further, embodiments of the disclosure have utility with different and various tool types and configurations.

What is claimed is:

1. A method for inserting a catheter into a vein of a patient, said method comprising:
    advancing a distal tip of a needle on a housing into the vein, wherein the catheter is disposed within a lumen of the needle while the distal tip is being advanced;
    pushing distally on a proximal connector on the catheter to distally advance a distal port of the catheter from the needle into the vein of the patient, wherein the proximal connector engages a proximal end of the housing;
    retracting the distal tip of the needle over the catheter and maintaining the distal tip of the needle in the housing while the distal port of the catheter remains in the vein of the patient;
    securing the housing to the patient while the distal tip of the needle remains in the housing; and
    attaching a fluid delivery tube to the proximal connector which is in fluid communication with a lumen of the catheter while the distal tip of the needle remains protected in the housing.

2. The method of claim 1, further comprising delivering fluid to the patient though the fluid delivery tube while the housing remains secured to the patient.

3. The method of claim 1, wherein retracting the needle over the catheter comprises releasing a constrained spring to axially translate the needle relative to the catheter.

4. The method of claim 3, wherein releasing the constrained spring to axially translate the needle relative to the catheter occurs automatically after the catheter has been fully advanced.

5. The method of claim 4, wherein the constrained spring comprises a constrained coil spring disposed coaxially over the needle held in place by a locking mechanism that is disengaged after the catheter has been fully advanced, allowing the constrained coil spring to axially expand to cause the needle to retract.

6. The method of claim 5, wherein the locking mechanism comprises a releasable latch, wherein the catheter releases the releasable latch to allow the needle to retract when the catheter is fully advanced within the needle lumen.

7. The method of claim 1, wherein retracting the needle over the catheter comprises manually retracting the needle by manually retracting a slider on the housing.

8. The method of claim 7, wherein the slider is coupled to a proximal end of the needle and mounted on an outer surface of the housing.

9. The method of claim 1, wherein the proximal connecter comprises luer on a proximal end of the catheter.

10. The method of claim 1, further comprising locking the catheter to the housing after the catheter has been fully advanced.

11. The method of claim 1, further comprising securing the proximal connector to the proximal end of the housing.

12. The method of claim 11, wherein securing the proximal connector to the proximal end of the housing comprises engaging threads on the proximal connector to threads on the proximal end of the housing.

13. The method of claim 11, wherein the proximal connector of the catheter comprises a female luer taper and a proximal portion of the housing comprises male luer threads, wherein the female luer taper and the male luer threads are joined to form a complete luer fitting when the catheter is fully advanced through the housing.

14. The method of claim 1, further comprising opening a valve in the proximal connector in response to engagement with an external connector on the fluid delivery tuber.

15. The catheter insertion apparatus of claim 14, wherein the valve in the proximal connector comprises a split valve that opens when advanced distally against a male fitting in an axial passage in the proximal connector on the catheter.

* * * * *